United States Patent
Chassot et al.

(10) Patent No.: US 7,455,698 B2
(45) Date of Patent: Nov. 25, 2008

(54) CATIONIC DYES AND DYESTUFF FOR KERATIN FIBRES CONTAINING SAID COMPOUNDS

(75) Inventors: Laurent Chassot, Praroman (CH); Laurence Descloux, Lovens (CH); Sylviane Oberson, Ecuvillens (CH); Gisela Umbricht, Marly (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 11/568,865

(22) PCT Filed: Apr. 4, 2005

(86) PCT No.: PCT/EP2005/003505

§ 371 (c)(1),
(2), (4) Date: Jun. 22, 2007

(87) PCT Pub. No.: WO2005/110995

PCT Pub. Date: Nov. 24, 2005

(65) Prior Publication Data

US 2007/0258929 A1    Nov. 8, 2007

(30) Foreign Application Priority Data

May 11, 2004    (DE) .................. 10 2004 023 122

(51) Int. Cl.
*A61Q 5/10*    (2006.01)
*C07D 231/00*    (2006.01)

(52) U.S. Cl. .................. 8/405; 8/406; 8/435; 8/570; 8/606; 548/371.4

(58) Field of Classification Search .................. 8/405, 8/406, 435, 570, 606; 548/371.4
See application file for complete search history.

(56) References Cited

U.S. PATENT DOCUMENTS 5,430,159 A    7/1995    Neunhoeffer et al.
5,931,973 A *    8/1999    Malle et al. ................ 8/431

FOREIGN PATENT DOCUMENTS

EP    1 398 021    3/2004

OTHER PUBLICATIONS

STIC Search Report dated Aug. 7, 2008.*
Hennig et al: "Azomethine, Azo and . . . " Jul. 14, 1986, Chemical Abstracts + Indexes, American Chemical Socienry. Columbus, US p. 78 (In English).

* cited by examiner

*Primary Examiner*—Eisa B Elhilo
(74) *Attorney, Agent, or Firm*—Michael J. Striker

(57) ABSTRACT

4-(Pyrazol-4-ylimino)-2,5-cyclohexadienylidene-ammonium salts of the general formula(I)

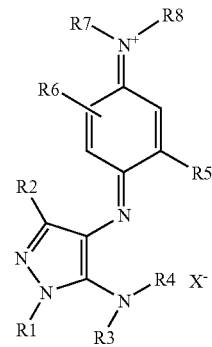

and colorants comprising these compounds for keratin fibres.

15 Claims, No Drawings

CATIONIC DYES AND DYESTUFF FOR KERATIN FIBRES CONTAINING SAID COMPOUNDS

FIELD OF THE INVENTION

The invention relates to novel 4-(pyrazol-4-ylimino)-2,5-cyclohexadienylidene-ammonium salts and to agents comprising these compounds for colouring keratin fibres.

BACKGROUND OF THE INVENTION

For the colour-changing treatment of keratin-containing fibres, for example human hair, wool or furs, use is usually made of two colouring methods. In the first method, the coloration is produced with so-called oxidative or permanent colorants, using a mixture of various developer substances and coupler substances and an oxidizing agent. If required, so-called direct (nonoxidative) dyes can be added to round off the colouring result or to produce particular colour effects. The second method uses exclusively direct dyes, which are applied to the fibres in a suitable carrier mass. This method is easy to use, exceptionally gentle and is characterized by low damage to the keratin fibres. The direct dyes used here are subject to a large number of requirements. For example, they have to be acceptable from a toxicological and dermatological point of view and allow the attainment of colorations in the desired intensity, which, inter alia, also requires adequate solubility in water. Furthermore, good lightfastness, acid fastness and rubbing fastness is required for the colorations achieved.

For a direct (nonoxidative) colorant for keratin fibres, a combination of different nonoxidative dyes is usually required. Since the choice of red and blue nonoxidative dyes which can be used in colorants for keratin fibres, in particular human hair, is limited, there is an urgent need to expand the dye palette which can be used.

SUMMARY OF THE INVENTION

In this regard, it has now surprisingly been found that novel 4-(pyrazol-4-ylimino)-2,5-cyclohexadienylidene-ammonium salts according to the general formula (I) are able to colour keratin fibres, such as, for example, hair, intense blue.

DETATILED DESCRIPTION OF THE INVENTION

The present invention therefore provides 4-(pyrazol-4-ylimino)-2,5-cyclohexadienylidene-ammonium salts of the general formula (I)

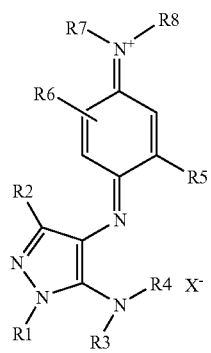

in which

R1 is a $C_1$-$C_6$-alkyl group, a $C_1$-$C_4$-hydroxyalkyl group, a $C_2$-$C_4$-dihydroxyalkyl group or a $C_2$-$C_6$-alkoxy-($C_1$-$C_2$)-alkyl group, a phenyl group, a benzyl group or a substituted benzyl group;

R3 and R4 independently of one another, are hydrogen, a $C_1$-$C_6$-alkyl group, a $C_1$-$C_4$-hydroxyalkyl group, a $C_2$-$C_4$-dihydroxyalkyl group or a $C_1$-$C_4$-alkoxy-($C_1$-$C_4$) alkyl group, or R3 and R4 together form a four-membered to eight-membered aliphatic ring;

R2 and R6, independently of one another, are hydrogen, a $C_1$-$C_4$-alkyl group, a $C_1$-$C_4$-hydroxyalkyl group, a phenyl group, a substituted phenyl group, a halogen atom or a substituted aminomethyl group;

R5 is a cyano group, a —NR10C(O)R11 group or a sulphonamide group;

R7 and R8, independently of one another, are a $C_1$-$C_6$-alkyl group, an unsaturated $C_3$-$C_6$-alkyl group, a $C_2$-$C_4$-hydroxyalkyl group, a $C_3$-$C_4$-dihydroxyalkyl group, a $C_2$-$C_4$-aminoalkyl group, a $C_2$-$C_4$-dimethylaminoalkyl group, a $C_2$-$C_4$-acetylaminoalkyl group, a $C_2$-$C_4$-methoxyalkyl group, a $C_2$-$C_4$-ethoxyalkyl group, a $C_1$-$C_4$-cyanoalkyl group, a $C_1$-$C_4$-carboxyalkyl group or a $C_1$-$C_4$-aminocarbonylalkyl group, or R7 and R8, together with the nitrogen atom, form a ring of the formula

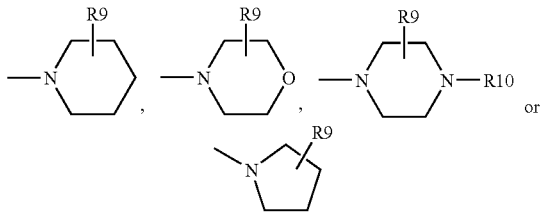

R9 is hydrogen or one or more hydroxyl groups, carboxyl groups, aminocarbonyl groups or hydroxymethyl groups;

R10 is hydrogen or a $C_1$-$C_6$-alkyl group;

R11 is hydrogen, a $C_1$-$C_6$-alkyl group, an amino group, an alkylamino group, a dialkylamino group, a phenyl group or a substituted phenyl group; and X⁻ is an anion, such as, for example, chloride, hydrogensulphate, sulphate, acetate or hexafluoro-phosphate.

Examples which can be specified are the following cationic compounds, which can be combined as desired with the abovementioned anions X— to be the electroneutral compounds of the formula (I):

(4-(5-amino-1-(4-methylphenyl)methyl-1H-pyrazol-4-ylimino)-3-acetamidocyclohexa-2,5-dienylidene)-diethylammonium, (4-(5-amino-1-(4-methyl-phenyl)methyl-1H-pyrazol-4-ylimino)-3-acetamidocyclohexa-2,5-dienylidene) diisopropylammonium, (4-(5-amino-1-(4-methylphenyl) methyl-1H-pyrazol-4-ylimino)-3-acetamidocyclohexa-2,5-dienylidene)dimethylammonium, 1-(4-(5-amino-1-(4-methylphenyl)methyl-1H-pyrazol-4-ylimino)-3-acetamidocyclohexa-2,5-dienylidene)-4-(hydroxymethyl) piperidinium, 1-(4-(5-amino-1-(4-methylphenyl)methyl-1H-pyrazol-4-ylimino)-3-acetamidocyclohexa-2,5-dienylidene)hydroxymethylpyrrolidinium, 1-(4-(5-amino-1-(4-methylphenyl)methyl-1H-pyrazol-4-ylimino)-3-acetamidocyclohexa-2,5-dienylidene)-4-hydroxypiperidinium, 1-(4-(5-amino-1-(4-methylphenyl) methyl-1H-pyrazol-4-ylimino)-3-acet-amidocyclohexa-2,5-dienylidene)-3-hydroxypyrrolidinium, 4-(4-(5-amino-1-(4-methylphenyl)methyl-1H-pyrazol-4-ylimino)-3-acetamidocyclohexa-2,5-dienylidene)morpholinium, 1-(4-

(5-amino-1-(4-methylphenyl)methyl-1H-pyrazol-4-ylimino)-3-acetamidocyclohexa-2,5-dienylidene)piperidinium, 1-(4-(5-amino-1-(4-methylphenyl)methyl-1H-pyrazol-4-ylimino)-3-acetamidocyclohexa-2,5-dienylidene)pyrrolidinium, (4-(5-amino-1-(4-methylphenyl)methyl-1H-pyrazol-4-ylimino)-3-methyl-sulphonamidocyclohexa-2,5-dienylidene) diethylammonium, (4-(5-amino-1-(4-methylphenyl)methyl-1H-pyrazol-4-ylimino)-3-methylsulphonamidocyclohexa-2,5-dienylidene)diisopropylammonium, (4-(5-amino-1-(4-methylphenyl)methyl-1H-pyrazol-4-ylimino)-3-methylsulphonamidocyclohexa-2,5-dienylidene)dimethylammonium, 1-(4-(5-amino-1-(4-methylphenyl)methyl-1H-pyrazol-4-ylimino)-3-methylsulphonamidocyclohexa-2,5-dienylidene)-3-(hydroxymethyl)piperidinium, 1-(4-(5-amino-1-(4-methylphenyl)methyl-1H-pyrazol-4-ylimino)-3-methylsulphonamidocyclohexa-2,5-dienylidene)-3-(hydroxy-methyl)pyrrolidinium, 1-(4-(5-amino-1-(4-methylphenyl)methyl-1H-pyrazol-4-ylimino)-3-methyl-sulphonamidocyclohexa-2,5-dienylidene)-3-hydroxy-piperidinium, 1-(4-(5-amino-1-(4-methylphenyl)methyl-1H-pyrazol-4-ylimino)-3-methylsulphonamidocyclohexa-2,5-dienylidene)-3-hydroxy-pyrrolidinium, (4-(5-amino-1-(4-methylphenyl)methyl-1H-pyrazol-4-ylimino)-3-methylsulphonamidocyclohexa-2,5-dienylidene)-3-morpholin-4-ium, 1-(4-(5-amino-1-(4-methylphenyl)methyl-1H-pyrazol-4-ylimino)-3-methylsulphonamidocyclohexa-2,5-dienylidene)piperidinium, 1-(4-(5-amino-1-(4-methylphenyl)methyl-1H-pyrazol-4-ylimino)-3-methyl-sulphonamidocyclohexa-2,5-dienylidene)pyrrolidinium, (4-(5-amino-1-(4-methylphenyl)methyl-1H-pyrazol-4-ylimino)-3-ureidocyclohexa-2,5-dienylidene)diethylammonium, (4-(5-amino-1-(4-methylphenyl)methyl-1H-pyrazol-4-ylimino)-3-ureidocyclohexa-2,5-dienylidene)diisopropylammonium, (4-(5-amino-1-(4-methylphenyl)methyl-1H-pyrazol-4-ylimino)-3-ureidocyclohexa-2,5-dienylidene)di(hydroxy-ethyl)ammonium, (4-(5-amino-1-(4-methylphenyl)methyl-1H-pyrazol-4-ylimino)-3-ureidocyclohexa-2,5-dienylidene) dimethylammonium, 1-(4-(5-amino-1-(4-methylphenyl)methyl-1H-pyrazol-4-ylimino)-3-ureidocyclohexa-2,5-dienylidene)-4-(hydroxymethyl)piperidinium, 1-(4-(5-amino-1-(4-methylphenyl)methyl-1H-pyrazol-4-ylimino)-3-ureidocyclohexa-2,5-dienylidene)hydroxy-methylpyrrolidinium, 1-(4-(5-amino-1-(4-methylphenyl)methyl-1H-pyrazol-4-ylimino)-3-ureidocyclohexa-2,5-dienylidene)-4-hydroxypiperidinium, 1-(4-(5-amino-1-(4-methylphenyl)methyl-1H-pyrazol-4-ylimino)-3-ureidocyclohexa-2,5-dienylidene)-3-hydroxypyrrolidinium, (4-(5-amino-1-(4-methylphenyl)methyl-1H-pyrazol-4-ylimino)-3-ureidocyclohexa-2,5-dienylidene)-3-morpholin-4-ium, 1-(4-(5-amino-1-(4-methylphenyl)methyl-1H-pyrazol-4-ylimino)-3-ureidocyclohexa-2,5-dienylidene)piperidinium, 1-(4-(5-amino-1-(4-methylphenyl)methyl-1H-pyrazol-4-ylimino)-3-ureidocyclohexa-2,5-dienylidene)pyrrolidinium, (4-(5-amino-1-(2-hydroxyethyl)-1H-pyrazol-4-ylimino)-3-acet-amidocyclohexa-2,5-dienylidene)diethylammonium, (4-(5-amino-1-(2-hydroxyethyl)-1H-pyrazol-4-ylimino)-3-acetamidocyclohexa-2,5-dienylidene)diisopropylammonium, (4-(5-amino-1-(2-hydroxyethyl)-1H-pyrazol-4-ylimino)-3-acetamidocyclohexa-2,5-dienylidene)dimethylammonium, 1-(4-(5-amino-1-(2-hydroxyethyl)-1H-pyrazol-4-ylimino)-3-acetamidocyclohexa-2,5-dienylidene)hydroxymethylpiperidinium, 1-(4-(5-amino-1-(2-hydroxyethyl)-1H-pyrazol-4-ylimino)-3-acet-amidocyclohexa-2,5-dienylidene)-3-(hydroxymethyl)-pyrrolidinium, 1-(4-(5-amino-1-(2-hydroxyethyl)-1H-pyrazol-4-ylimino)-3-acetamidocyclohexa-2,5-dienyl-idene)-3-hydroxypiperidinium, 1-(4-(5-amino-1-(2-hydroxyethyl)-1H-pyrazol-4-ylimino)-3-acetamidocyclohexa-2,5-dienylidene)-3-hydroxypyrrolidinium, (4-(5-amino-1-(2-hydroxyethyl)-1H-pyrazol-4-ylimino)-3-acetamidocyclohexa-2,5-dienylidene)morpholiniun, 1-(4-(5-amino-1-(2-hydroxyethyl)-1H-pyrazol-4-ylimino)-3-acetamidocyclohexa-2,5-dienylidene)piperidinium, 1-(4-(5-amino-1-(2-hydroxyethyl)-1H-pyrazol-4-ylimino)-3-acetamidocyclohexa-2,5-dienylidene)pyrrolidinium, (4-(5-amino-1-(2-hydroxyethyl)-1H-pyrazol-4-ylimino)-3-methylsulphonamidocyclohexa-2,5-dienylidene) diethylammonium, (4-(5-amino-1-(4-methylphenyl)methyl-1H-pyrazol-4-ylimino)-3-methyl-sulphonamidocyclohexa-2,5-dienylidene)di(hydroxyethyl)ammonium, (4-(5-amino-1-(2-hydroxyethyl)-1H-pyrazol-4-ylimino)-3-methylsulphon-amidocyclohexa-2,5-dienylidene) diisopropylammonium, (4-(5-amino-1-(2-hydroxyethyl)-1H-pyrazol-4-ylimino)-3-methylsulphonamidocyclohexa-2,5-dienylidene)dimethylammonium, 1-(4-(5-amino-1-(2-hydroxyethyl)-1H-pyrazol-4-ylimino)-3-methylsulphon-amidocyclohexa-2,5-dienylidene)-3-(hydroxymethyl)piperidinium, 1-(4-(5-amino-1-(2-hydroxyethyl)-1H-pyrazol-4-ylimino)-3-methylsulphonamidocyclohexa-2,5-dienylidene)-3-(hydroxymethyl)pyrrolidinium, 1-(4-(5-amino-1-(2-hydroxyethyl)-1H-pyrazol-4-ylimino)-3-methylsulphonamidocyclohexa-2,5-dienylidene)-4-hydroxypiperidinium, 1-(4-(5-amino-1-(2-hydroxyethyl)-1H-pyrazol-4-ylimino)-3-methylsulphonamidocyclohexa-2,5-dienylidene)-3-hydroxypyrrolidinium, 4-(4-(5-amino-1-(2-hydroxyethyl)-1H-pyrazol-4-ylimino)-3-methylsulphonamidocyclohexa-2,5-dienylidene) morpholinium, 1-(4-(5-amino-1-(2-hydroxyethyl)-1H-pyrazol-4-ylimino)-3-methylsulphon-amidocyclohexa-2,5-dienylidene)piperidinium, 1-(4-(5-amino-1-(2-hydroxyethyl)-1H-pyrazol-4-ylimino)-3-methylsulphonamidocyclohexa-2,5-dienylidene)pyrrolidinium, (4-(5-amino-1-(2-hydroxyethyl)-1H-pyrazol-4-ylimino)-3-ureidocyclohexa-2t 5-dienylidene) diethylammonium, (4-(5-amino-1-(2-hydroxyethyl)-1H-pyrazol-4-ylimino)-3-ureidocyclohexa-2,5-dienylidene) diisopropylammonium, (4-(5-amino-1-(2-hydroxyethyl)-1H-pyrazol-4-ylimino)-3-ureidocyclohexa-2,5-dienylidene) dimethylammonium, 1-(4-(5-amino-1-(2-hydroxyethyl)-1H-pyrazol-4-ylimino)-3-ureidocyclohexa-2,5-dienylidene)-4-(hydroxymethyl)piperidinium, 1-(4-(5-amino-1-(2-hydroxyethyl)-1H-pyrazol-4-ylimino)-3-ureidocyclohexa-2,5-dienylidene)-3-(hydroxymethyl)-pyrrolidinium, 1-(4-(5-amino-1-(2-hydroxyethyl)-1H-pyrazol-4-ylimino)-3-ureidocyclohexa-2,5-dienylidene) hydroxypiperidinium, 1-(4-(5-amino-1-(2-hydroxyethyl)-1H-pyrazol-4-ylimino)-3-ureidocyclohexa-2,5-dienylidene)-3-hydroxypyrrolidinium, 4-(4-(5-amino-1-(2-hydroxyethyl)-1H-pyrazol-4-ylimino)-3-ureidocyclohexa-2,5-dienylidene)morpholinium, 1-(4-(5-amino-1-(2-hydroxyethyl)-1H-pyrazol-4-ylimino)-3-ureidocyclohexa-2,5-dienylidene)piperidinium, 1-(4-(5-amino-1-(2-hydroxyethyl)-1H-pyrazol-4-ylimino)-3-ureidocyclohexa-2,5-dienylidene)pyrrolidinium, (4-(5-amino-1-ethyl-1H-pyrazol-4-ylimino)-3-acetamidocyclohexa-2,5-dienylidene)diethylammonium, (4-(5-amino-1-ethyl-1H-pyrazol-4-ylimino)-3-acetamidocyclohexa-2,5-dienylidene)diisopropylammonium, (4-(5-amino-1-ethyl-1H-pyrazol-4-ylimino)-3-acetamidocyclohexa-2,5-dienylidene)dimethylammonium, 1-(4-(5-amino-1-ethyl-1H-pyrazol-4-ylimino)-3-acetamidocyclohexa-2,5-dienylidene)-4- hydroxymethylpiperidinium, 1-(4-(5-amino-1-ethyl-1H-pyrazol-4-ylimino)-3-acetamidocyclohexa-2,5-dienylidene)-3-(hydroxymethyl)pyrrolidinium, 1-(4-(5-amino-1-ethyl-1H-pyrazol-4-ylimino)-3-acetamidocyclohexa-2,5-dienylidene)-4-hydroxypiperidinium, 1-(4-(5-amino-1-ethyl-1H-pyrazol-4-ylimino)-3-acetamidocyclohexa-2,5-dienylidene)-3-hydroxypyrrolidinium, (4-(5-amino-1-ethyl-1H-pyrazol-4-ylimino)-3-acetamidocyclohexa-2,5-dienylidene)-3-morpholin-4-ium, 1-(4-(5-amino-1-ethyl-1H-pyrazol-4-ylimino)-3-acetamidocyclohexa-2,5-dienylidene)piperidinium, 1-(4-(5-amino-1-ethyl-1H-pyrazol-4-ylimino)-3-acetamidocyclohexa-2,5-dienylidene)pyrrolidinium, (4-(5-amino-1-ethyl-1H-pyrazol-4-ylimino)-3-methylsulphonamidocyclohexa-2,5-dienylidene)diethylammonium, (4-(5-amino-1-ethyl-1H-pyrazol-4-ylimino)-3-methylsulphonamidocyclohexa-2,5-dienylidene)diisopropylammonium, (4-(5-amino-1-ethyl-1H-pyrazol-4-ylimino)-3-methylsulphonamidocyclohexa-2,5-dienylidene)dimethylammonium, 1-(4-(5-amino-1-ethyl-1H-pyrazol-4-ylimino)-3-methyl-sulphonamidocyclohexa-2,5-dienylidene)-4-hydroxymethyl-piperidinium, 1-(4-(5-amino-1-ethyl-1H-pyrazol-4-ylimino)-3-methylsulphonamidocyclohexa-2,5-dienylidene)-3-(hydroxymethyl)pyrrolidinium, 1-(4-(5-amino-1-ethyl-1H-pyrazol-4-ylimino)-3-methylsulphonamidocyclohexa-2,5-dienylidene)-4-hydroxypiperidinium, 1-(4-(5-amino-1-ethyl-1H-pyrazol-4-ylimino)-3-methylsulphonamidocyclohexa-2,5-dienylidene)hydroxypyrrolidinium, 4-(4-(5-amino-1-ethyl-1H-pyrazol-4-ylimino)-3-methylsulphonamidocyclohexa-2,5-dienylidene)morpholinium, 1-(4-(5-amino-1-ethyl-1H-pyrazol-4-ylimino)-3-methylsulphonamidocyclohexa-2,5-dienylidene)piperidinium, 1-(4-(5-amino-1-ethyl-1H-pyrazol-4-ylimino)-3-methylsulphonamidocyclohexa-2,5-dienylidene)pyrrolidinium, (4-(5-amino-1-ethyl-1H-pyrazol-4-ylimino)-3-ureidocyclohexa-2,5-dienylidene)diethylammonium, (4-(5-amino-1-ethyl-1H-pyrazol-4-ylimino)-3-ureidocyclohexa-2,5-dienylidene)diisopropylammonium, (4-(5-amino-1-ethyl-1H-pyrazol-4-ylimino)-3-ureidocyclohexa-2,5-dienylidene)dimethylammonium, 1-(4-(5-amino-1-ethyl-1H-pyrazol-4-ylimino)-3-ureidocyclohexa-2,5-dienylidene)hydroxymethylpiperidinium, 1-(4-(5-amino-1-ethyl-1H-pyrazol-4-ylimino)-3-ureidocyclohexa-2,5-dienylidene)-hydroxymethylpyrrolidinium, 1-(4-(5-amino-1-ethyl-1H-pyrazol-4-ylimino)-3-ureidocyclohexa-2,5-dienylidene)-4-hydroxypiperidinium, 1-(4-(5-amino-1-ethyl-1H-pyrazol-4-ylimino)-3-ureidocyclohexa-2,5-dien-ylidene)-3-hydroxypyrrolidinium, 4-(4-(5-amino-1-ethyl-1H-pyrazol-4-ylimino)-3-ureidocyclohexa-2,5-dienylidene)morpholinium, 1-(4-(5-amino-1-ethyl-1H-pyrazol-4-ylimino)-3-ureidocyclohexa-2,5-dienylidene)piperidinium, 1-(4-(5-amino-1-ethyl-1H-pyrazol-4-ylimino)-3-ureidocyclohexa-2,5-dienylidene)pyrrolidinium, (4-(5-amino-1-isopropyl-1H-pyrazol-4-ylimino)-3-acetamidocyclohexa-2,5-dienylidene)diethylammonium, (4-(5-amino-1-isopropyl-1H-pyrazol-4-ylimino)-3-acetamidocyclohexa-2,5-dienylidene)diisopropylammonium, (4-(5-amino-1-isopropyl-1H-pyrazol-4-ylimino)-3-acetamidocyclohexa-2,5-dienylidene)dimethylammonium, 1-(4-(5-amino-1-isopropyl-1H-pyrazol-4-ylimino)-3-acetamidocyclohexa-2,5-dienylidene)-3-(hydroxymethyl)piperidinium, 1-(4-(5-amino-1-isopropyl-1H-pyrazol-4-ylimino)-3-acetamidocyclohexa-2,5-dienylidene)-3-(hydroxymethyl)pyrrolidinium, 1-(4-(5-amino-1-isopropyl-1H-pyrazol-4-ylimino)-3-acetamidocyclohexa-2,5-dienylidene)-4-hydroxypiperidinium, 1-(4-(5-amino-1-isopropyl-1H-pyrazol-4-ylimino)-3-acetamidocyclohexa-2,5-dienylidene)-3-hydroxypyrrolidinium, 4-(4-(5-amino-1-isopropyl-1H-pyrazol-4-ylimino)-3-acetamidocyclohexa-2,5-dienylidene)morpholinium, 1-(4-(5-amino-1-isopropyl-1H-pyrazol-4-ylimino)-3-acetamidocyclohexa-2,5-dienylidene)piperidinium, 1-(4-(5-amino-1-isopropyl-1H-pyrazol-4-ylimino)-3-acetamidocyclohexa-2,5-dienylidene)pyrrolidinium, (4-(5-amino-1-isopropyl-1H-pyrazol-4-ylimino)-3-methylsulphonamidocyclohexa-2,5-dienylidene)diethylammonium, (4-(5-amino-1-isopropyl-1H-pyrazol-4-ylimino)-3-methylsulphonamidocyclohexa-2,5-dienylidene)diisopropylammonium, (4-(5-amino-1-isopropyl-1H-pyrazol-4-ylimino)-3-methylsulphonamidocyclohexa-2,5-dienylidene)dimethylammonium, 1-(4-(5-amino-1-isopropyl-1H-pyrazol-4-ylimino)-3-methylsulphonamidocyclohexa-2,5-dienylidene)hydroxymethylpiperidinium, 1-(4-(5-amino-1-isopropyl-1H-pyrazol-4-ylimino)-3-methylsulphon-amidocyclohexa-2,5-dienylidene)-3-(hydroxymethyl)-pyrrolidinium, 1-(4-(5-amino-1-isopropyl-1H-pyrazol-4-ylimino)-3-methylsulphonamidocyclohexa-2,5-dienylidene)-4-hydroxypiperidinium, 1-(4-(5-amino-1-isopropyl-1H-pyrazol-4-ylimino)-3-methylsulphonamidocyclohexa-2,5-dienylidene)-3-hydroxy-pyrrolidinium, 4-(4-(5-amino-1-isopropyl-1H-pyrazol-4-ylimino)-3-methylsulphonamidocyclohexa-2,5-dienylidene)morpholinium, 1-(4-(5-amino-1-isopropyl-1H-pyrazol-4-ylimino)-3-methylsulphonamidocyclohexa-2,5-dienylidene)piperidinium, 1-(4-(5-amino-1-isopropyl-1H-pyrazol-4-ylimino)-3-methylsulphonamidocyclohexa-2,5-dienylidene)pyrrolidinium, (4-(5-amino-1-isopropyl-1H-pyrazol-4-ylimino)-3-ureidocyclohexa-2,5-dienylidene)diethylammonium, (4-(5-amino-1-isopropyl-1H-pyrazol-4-ylimino)-3-ureidocyclohexa-2,5-dienylidene)diisopropylammonium, (4-(5-amino-1-isopropyl-1H-pyrazol-4-ylimino)-3-ureidocyclohexa-2,5-dienylidene)dimethylammonium, 1-(4-(5-amino-1-isopropyl-1H-pyrazol-4-ylimino)-3-ureidocyclohexa-2,5-dienylidene)-4-(hydroxymethyl)piperidinium, 1-(4-(5-amino-1-isopropyl-1H-pyrazol-4-ylimino)-3-ureidocyclohexa-2,5-dienylidene)-3-(hydroxymethyl)pyrrolidinium, 1-(4-(5-amino-1-isopropyl-1H-pyrazol-4-ylimino)-3-ureidocyclohexa-2,5-dienylidene)-4-hydroxypiperidinium, 1-(4-(5-amino-1-isopropyl-1H-pyrazol-4-ylimino)-3-ureidocyclohexa-2,5-dienylidene)-3-hydroxypyrrolidinium, 4-(4-(5-amino-1-isopropyl-1H-pyrazol-4-ylimino)-3-ureidocyclohexa-2,5-dienylidene)-morpholinium, 1-(4-(5-amino-1-isopropyl-1H-pyrazol-4-ylimino)-3-ureidocyclohexa-2,5-dienylidene)piperidinium, 1-(4-(5-amino-1-isopropyl-1H-pyrazol-4-ylimino)-3-ureidocyclohexa-2,5-dienylidene)pyrrolidinium, (4-(5-amino-1-methyl-1H-pyrazol-4-ylimino)-3-acetamidocyclohexa-2,5-dienylidene)diethylammonium, (4-(5-amino-1-methyl-1H-pyrazol-4-ylimino)-3-acetamidocyclohexa-2,5-dienylidene)diisopropylammonium, (4-(5-amino-1-methyl-1H-pyrazol-4-ylimino)-3-acetamidocyclohexa-2,5-dienylidene)dimethylammonium, 1-(4-(5-amino-1-methyl-1H-pyrazol-4-ylimino)-3-acetamidocyclohexa-2,5-dienylidene)hydroxy-methylpiperidinium, 1-(4-(5-amino-1-methyl-1H-pyrazol-4-ylimino)-3-acetamidocyclohexa-2,5-dienylidene)-3-(hydroxymethyl)pyrrolidinium, 1-(5-amino-1-methyl-1H-pyrazol-4-ylimino)-3-acetamidocyclohexa-2,5-dienylidene)-4-hydroxypiperidinium, 1-(4-(5-amino-1-methyl-1H-pyrazol-4-ylimino)-3-acetamidocyclohexa-2,5-dienylidene)-3-hydroxypyrrolidinium, 4-(4-(5-amino-1-methyl-1H-pyrazol-4-ylimino)-3-acetamidocyclohexa-2,5- dienylidene)morpholinium, 1-(4-(5-amino-1-methyl-1H-pyrazol-4-ylimino)-3-acetamidocyclohexa-2,5-dienylidene)piperidinium, 1-(4-(5-amino-1-methyl-1H-pyrazol-4-ylimino)-3-acetamidocyclohexa-2,5-dienylidene)pyrrolidinium, (4-(5-amino-1-methyl-1H-pyrazol-4-ylimino)-3-methylsulphonamidocyclohexa-2,5-dienylidene)diethylammonium, (4-(5-amino-1-methyl-1H-pyrazol-4-ylimino)-3-methylsulphonamidocyclohexa-2,5-dienylidene)diisopropylammonium, (4-(5-amino-1-methyl-1H-pyrazol-4-ylimino)-3-methylsulphonamidocyclohexa-2,5-dienylidene)dimethylammonium, 1-(4-(5-amino-1-methyl-1H-pyrazol-4-ylimino)-3-methyl-sulphonamidocyclohexa-2,5-dienylidene)hydroxy-methylpiperidinium, 1-(4-(5-amino-1-methyl-1H-pyrazol-4-ylimino)-3-methylsulphonamidocyclohexa-2,5-dienyl-idene)-3-(hydroxymethyl)pyrrolidinium, 1-(4-(5-amino-1-methyl-1H-pyrazol-4-ylimino)-3-methylsulphon-amidocyclohexa-2,5-dienylidene)-4-hydroxypiperidinium, 1-(4-(5-amino-1-methyl-1H-pyrazol-4-ylimino)-3-methylsulphonamidocyclohexa-2,5-dienylidene)-3-hydroxypyrrolidinium, 4-(4-(5-amino-1-methyl-1H-pyrazol-4-ylimino)-3-methylsulphonamidocyclohexa-2,5-dienylidene)morpholinium, 1-(4-(5-amino-1-methyl-1H-pyrazol-4-ylimino)-3-methylsulphonamidocyclohexa-2,5-dienylidene)piperidinium, 1-(4-(5-amino-1-methyl-1H-pyrazol-4-ylimino)-3-methylsulphonamidocyclohexa-2,5-dienylidene)pyrrolidinium, (4-(5-amino-1-methyl-1H-pyrazol-4-ylimino)-3-ureidocyclohexa-2,5-dienylidene)diethylammonium, (4-(5-amino-1-methyl-1H-pyrazol-4-ylimino)-3-ureidocyclohexa-2,5-dienylidene)diisopropylammonium, (4-(5-amino-1-methyl-1H-pyrazol-4-ylimino)-3-ureidocyclohexa-2,5-dien-ylidene)dimethylammonium, 1-(4-(5-amino-1-methyl-1H-pyrazol-4-ylimino)-3-ureidocyclohexa-2,5-dienylidene)-4-(hydroxymethyl)piperidinium, 1-(4-(5-amino-1-methyl-1H-pyrazol-4-ylimino)-3-ureidocyclohexa-2,5-dienylidene)hydroxymethylpyrrolidinium, 1-(4-(5-amino-1-methyl-1H-pyrazol-4-ylimino)-3-ureidocyclohexa-2,5-dienylidene)-4-hydroxypiperidinium, (4-(5-amino-1-methyl-1H-pyrazol-4-ylimino)-3-ureidocyclohexa-2,5-dienylidene)hydroxy, 4-(4-(5-amino-1-methyl-1H-pyrazol-4-ylimino)-3-ureidocyclohexa-2,5-dienylidene)-morpholinium, 1-(4-(5-amino-1-methyl-1H-pyrazol-4-ylimino)-3-ureidocyclohexa-2,5-dienylidene)piperidinium, 1-(4-(5-amino-1-methyl-1H-pyrazol-4-ylimino)-3-ureidocyclohexa-2,5-dienyl-idene)pyrrolidinium, (4-(5-amino-1-phenyl-1H-pyrazol-4-ylimino)-3-acetamidocyclohexa-2,5-dien-ylidene)diethylammonium, (4-(5-amino-1-phenyl-1H-pyrazol-4-ylimino)-3-acetamidocyclohexa-2,5-dienylidene)diisopropylammonium, (4-(5-amino-1-phenyl-1H-pyrazol-4-ylimino)-3-acetamidocyclohexa-2,5-dienyl-idene)dimethylammonium, 1-(4-(5-amino-1-phenyl-1H-pyrazol-4-ylimino)-3-acetamidocyclohexa-2,5-dienylidene)-4-(hydroxymethyl)piperidinium, 1-(4-(5-amino-1-phenyl-1H-pyrazol-4-ylimino)-3-acetamidocyclohexa-2,5-dienylidene)-3-(hydroxymethyl)pyrrolidinium, 1-(4-(5-amino-1-phenyl-1H-pyrazol-4-ylimino)-3-acetamidocyclohexa-2,5-dienylidene)-4-hydroxypiperidinium, 1-(4-(5-amino-1-phenyl-1H-pyrazol-4-ylimino)-3-acetamidocyclohexa-2,5-dienylidene)-3-hydroxypyrrolidinium, 4-(4-(5-amino-1-phenyl-1H-pyrazol-4-ylimino)-3-acetamidocyclohexa-2,5-dienylidene)morpholin-4-ium, 1-(4-(5-amino-1-phenyl-1H-pyrazol-4-ylimino)-3-acetamidocyclohexa-2,5-dienylidene)piperidinium, 1-(4-(5-amino-1-phenyl-1H-pyrazol-4-ylimino)-3-acetamidocyclohexa-2,5-dienylidene)pyrrolidinium, (4-(5-amino-1-phenyl-1H-pyrazol-4-ylimino)-3-methylsulphonamidocyclohexa-2,5-dienylidene)diethylammonium, (4-(5-amino-1-phenyl-1H-pyrazol-4-ylimino)-3-methylsulphonamidocyclohexa-2,5-dienylidene)diisopropylammonium, (4-(5-amino-1-phenyl-1H-pyrazol-4-ylimino)-3-methylsulphonamidocyclohexa-2,5-dienylidene)dimethylammonium, 1-(4-(5-amino-1-phenyl-1H-pyrazol-4-ylimino)-3-methylsulphonamidocyclohexa-2,5-dienylidene)-4-(hydroxymethyl)piperidinium, 1-(4-(5-amino-1-phenyl-1H-pyrazol-4-ylimino)-3-methylsulphonamidocyclohexa-2,5-dienylidene)-3-(hydroxymethyl)pyrrolidinium, 1-(4-(5-amino-1-phenyl-1H-pyrazol-4-ylimino)-3-methylsulphonamidocyclohexa-2,5-dienylidene)-4-hydroxypiperidinium, 1-(4-(5-amino-1-phenyl-1H-pyrazol-4-ylimino)-3-methylsulphonamidocyclohexa-2,5-dienylidene)-3-hydroxypyrrolidinium, 4-(4-(5-amino-1-phenyl-1H-pyrazol-4-ylimino)-3-methylsulphonamidocyclohexa-2,5-dienylidene)morpholinium, 1-(4-(5-amino-1-phenyl-1H-pyrazol-4-ylimino)-3-methylsulphonamidocyclohexa-2,5-dienylidene)piperidinium, 1-(4-(5-amino-1-phenyl-1H-pyrazol-4-ylimino)-3-methylsulphonamidocyclohexa-2,5-dienylidene)pyrrolidinium, (4-(5-amino-1-phenyl-1H-pyrazol-4-ylimino)-3-ureidocyclohexa-2,5-dienylidene)-diethylammonium, (4-(5-amino-1-phenyl-1H-pyrazol-4-ylimino)-3-ureidocyclohexa-2,5-dienyl-idene)diisopropylammonium, (4-(5-amino-1-phenyl-1H-pyrazol-4-ylimino)-3-ureidocyclohexa-2,5-dienylidene)dimethylammonium, 1-(4-(5-amino-1-phenyl-1H-pyrazol-4-ylimino)-3-ureidocyclohexa-2,5-dienylidene)-4-(hydroxymethyl)piperidinium, 1-(4-(5-amino-1-phenyl-1H-pyrazol-4-ylimino)-3-ureidocyclohexa-2,5-dienylidene)-3-(hydroxymethyl)pyrrolidinium, 1-(4-(5-amino-1-phenyl-1H-pyrazol-4-ylimino)-3-ureidocyclohexa-2,5-dienylidene)hydroxypiperidinium, 1-(4-(5-amino-1-phenyl-1H-pyrazol-4-ylimino)-3-ureidocyclohexa-2,5-dienylidene)-3-hydroxypyrrolidinium, 4-(4-(5-amino-1-phenyl-1H-pyrazol-4-ylimino)-3-ureidocyclohexa-2,5-dienylidene)morpholinium, 1-(4-(5-amino-1-phenyl-1H-pyrazol-4-ylimino)-3-ureidocyclohexa-2,5-dienylidene)piperidinium, 1-(4-(5-amino-1-phenyl-1H-pyrazol-4-ylimino)-3-ureidocyclohexa-2,5-dienylidene)pyrrolidinium, (4-(3-methyl-5-amino-1-(2-hydroxyethyl)-1H-pyrazol-4-ylimino)-3-acetamidocyclohexa-2,5-dienylidene)diethylammonium, 1-(4-(3-methyl-5-amino-1-(2-hydroxyethyl)-1H-pyrazol-4-ylimino)-3-acetamidocyclohexa-2,5-dienylidene)pyrrolidinium, (4-(3-methyl-5-amino-1-(2-hydroxyethyl)-1H-pyrazol-4-ylimino)-3-methylsulphonamidocyclohexa-2,5-dienylidene)diethylammonium, 1-(4-(3-methyl-5-amino-1-(2-hydroxyethyl)-1H-pyrazol-4-ylimino)-3-methylsulphonamidocyclohexa-2,5-dienylidene)pyrrolidinium, (4-(3-methyl-5-amino-1-(2-hydroxyethyl)-1H-pyrazol-4-ylimino)-3-ureidocyclohexa-2,5-dienyl-idene)diethylammonium, 1-(4-(3-methyl-5-amino-1-(2-hydroxyethyl)-1H-pyrazol-4-ylimino)-3-ureidocyclohexa-2,5-dienylidene)pyrrolidinium, (4-(3-methyl-5-amino-1-isopropyl-1H-pyrazol-4-ylimino)-3-acetamidocyclohexa-2,5-dienylidene)diethylammonium, 1-(4-(3-methyl-5-amino-1-isopropyl-1H-pyrazol-4-ylimino)-3-acetamidocyclohexa-2,5-dienylidene)pyrrolidinium, (4-(3-methyl-5-amino-1-isopropyl-1H-pyrazol-4-ylimino)-3-methylsulphonamidocyclohexa-2,5-dienylidene)diethylammonium, 1-(4-(3-methyl-5-amino-1-isopropyl-1H-pyrazol-4-ylimino)-3-methylsulphonamidocyclohexa-2,5-dienylidene)pyrrolidinium, (4-(3-methyl-5-amino-1-isopropyl-1H-pyrazol-4-ylimino)-3-ureidocyclohexa-2,5-dienylidene)diethylammonium, 1-(4-(3-methyl-5-amino-1-isopropyl-1H-pyrazol-4-ylimino)-3-ureidocyclohexa-2,5- dienylidene)pyrrolidinium, 1-(4-(3-phenyl-5-amino-1-(2-hydroxyethyl)-1H-pyrazol-4-ylimino)-3-acetamidocyclohexa-2,5-dienylidene)diethylammonium, 1-(4-(3-phenyl-5-amino-1-(2-hydroxyethyl)-1H-pyrazol-4-ylimino)-3-acetamidocyclohexa-2,5-dienylidene)pyrrolidinium, (4-(3-phenyl-5-amino-1-(2-hydroxyethyl)-1H-pyrazol-4-ylimino)-3-methylsulphon-amidocyclohexa-2,5-dienylidene)diethylammonium, 1-(4-(3-phenyl-5-amino-1-(2-hydroxyethyl)-1H-pyrazol-4-ylimino)-3-methylsulphonamidocyclohexa-2,5-dienylidene)pyrrolidinium, (4-(3-phenyl-5-amino-1-(2-hydroxyethyl)-1H-pyrazol-4-ylimino)-3-ureidocyclohexa-2,5-dienylidene)diethylammonium, 1-(4-(3-phenyl-5-amino-1-(2-hydroxyethyl)-1H-pyrazol-4-ylimino)-3-ureidocyclohexa-2,5-dienylidene)pyrrolidinium, (4-(3-phenyl-5-amino-1-isopropyl-1H-pyrazol-4-ylimino)-3-acetamidocyclohexa-2,5-dienylidene)diethylammonium, 1-(4-(3-phenyl-5-amino-1-isopropyl-1H-pyrazol-4-ylimino)-3-acetamidocyclohexa-2,5-dienylidene)pyrrolidinium, (4-(3-phenyl-5-amino-1-isopropyl-1H-pyrazol-4-ylimino)-3-methylsulphonamidocyclohexa-2,5-dienylidene)diethylammonium, 1-(4-(3-phenyl-5-amino-1-isopropyl-1H-pyrazol-4-ylimino)-3-methylsulphonamidocyclohexa-2,5-dienylidene)pyrrolidinium, (4-(5-amino-1-(2-hydroxyethyl)-1H-pyrazol-4-ylimino)-3-ureidocyclohexa-2,5-dienylidene)di(2-hydroxyethyl)ammonium, (4-(5-amino-1-(2-hydroxyethyl)-1H-pyrazol-4-ylimino)-3-methylsulphonamidocyclohexa-2,5-dienylidene)di(2-hydroxyethyl)ammonium, (4-(5-amino-1-(4-methylphenyl)methyl-1H-pyrazol-4-ylimino)-3-ureidocyclohexa-2,5-dienylidene)di(2-hydroxyethyl)ammonium, (4-(5-amino-1-(4-methylphenyl)methyl-1H-pyrazol-4-ylimino)-3-methylsulphonamidocyclohexa-2,5-dienylidene)di(2-hydroxyethyl)ammonium, (4-(5-amino-1-isopropyl-1H-pyrazol-4-ylimino)-3-ureidocyclohexa-2,5-dienylidene)di(2-hydroxyethyl)ammonium, (4-(5-amino-1-isopropyl-1H-pyrazol-4-ylimino)-3-methylsulphonamidocyclohexa-2,5-dienylidene)di(2-hydroxyethyl)ammonium, (4-(5-amino-1-(2-hydroxyethyl)-1H-pyrazol-4-ylimino)-3-ureidocyclohexa-2,5-dienylidene)di(2-hydroxyethyl)ammonium, (4-(5-amino-1-(2-hydroxyethyl)-1H-pyrazol-4-ylimino)-3-methyl-sulphonamidocyclohexa-2,5-dienylidene)di(2-hydroxyethyl)ammonium, (4-(5-amino-1-(4-methylphenyl)methyl-1H-pyrazol-4-ylimino)-3-ureidocyclohexa-2,5-dienylidene)di(2-hydroxyethyl)ammonium, (4-(5-amino-1-(4-methylphenyl)methyl-1H-pyrazol-4-ylimino)-3-methyl-sulphonamidocyclohexa-2,5-dienylidene)di(2-hydroxy-ethyl)ammonium, (4-(5-amino-1-isopropyl-1H-pyrazol-4-ylimino)-3-ureidocyclohexa-2,5-dienylidene)di(2-hydroxyethyl)ammonium and (4-(5-amino-1-isopropyl-1H-pyrazol-4-ylimino)-3-methylsulphonamidocyclohexa-2,5-dienylidene)di(2-hydroxyethyl)ammonium.

Preference is given to compounds of the formula (I) in which (i) one or more of the radicals R2, R3, R4 and R6 are hydrogen, (ii) R1 is a $C_1$-$C_6$-alkyl group, a $C_1$-$C_4$-hydroxyalkyl group, a benzyl group or methylbenzyl group and R2, R3, R4 and R6 are hydrogen at the same time and/or (iii) R5 is an amino group, an —NHC(O)R11 group or a sulphonamide group and R6 is a hydrogen and/or (iv) R7 and R8 are a $C_1$-$C_3$-alkyl group (in particular a methyl group) or, together with the nitrogen atom, form a pyrrolidine ring.

In particular, mention is made of the salts of the following compounds:

(4-(5-amino-1-(2-hydroxyethyl)-1H-pyrazol-4-ylimino)-3-ureidocyclohexa-2,5-dienylidene)dimethylammonium, (4-(5-amino-1-(2-hydroxyethyl)-1H-pyrazol-4-ylimino)-3-ureidocyclohexa-2,5-dienylidene)diethylammonium, (4-(5-amino-1-(2-hydroxyethyl)-1H-pyrazol-4-ylimino)-3-ureidocyclohexa-2,5-dienylidene)di(2-hydroxyethyl)-ammonium, 1-(4-(5-amino-1-(2-hydroxyethyl)-1H-pyrazol-4-ylimino)-3-ureidocyclohexa-2,5-dienylidene)-hydroxymethylpiperidinium, 1-(4-(5-amino-1-(2-hydroxyethyl)-1H-pyrazol-4-ylimino)-3-ureidocyclohexa-2,5-dienylidene)hydroxymethylpyrrolidinium, 1-(4-(5-amino-1-(2-hydroxyethyl)-1H-pyrazol-4-ylimino)-3-ureidocyclohexa-2,5-dienylidene)-4-hydroxypiperidinium, 1-(4-(5-amino-1-(2-hydroxyethyl)-1H-pyrazol-4-ylimino)-3-ureidocyclohexa-2,5-dienylidene)-3-hydroxypyrrolidinium, 4-(4-(5-amino-1-(2-hydroxyethyl)-1H-pyrazol-4-ylimino)-3-ureidocyclohexa-2,5-dienylidene)morpholinium, 1-(4-(5-amino-1-(2-hydroxyethyl)-1H-pyrazol-4-ylimino)-3-ureidocyclohexa-2,5-dienylidene)piperidinium, 1-(4-(5-amino-1-(2-hydroxyethyl)-1H-pyrazol-4-ylimino)-3-ureidocyclohexa-2,5-dienylidene)pyrrolidinium, (4-(5-amino-1-(2-hydroxyethyl)-1H-pyrazol-4-ylimino)-3-methylsulphonamidocyclohexa-2,5-dienylidene)dimethyl-ammonium, (4-(5-amino-1-(2-hydroxyethyl)-1H-pyrazol-4-ylimino)-3-methylsulphonamidocyclohexa-2,5-dienylidene)diethylammonium, (4-(5-amino-1-(2-hydroxyethyl)-1H-pyrazol-4-ylimino)-3-methylsulphon-amidocyclohexa-2,5-dienylidene)di(2-hydroxyethyl)-ammonium, 1-(4-(5-amino-1-(2-hydroxyethyl)-1H-pyrazol-4-ylimino)-3-methylsulphonamidocyclohexa-2,5-dienylidene)-2-(hydroxymethyl)piperidinium, i-(4-(5-amino-1-(2-hydroxyethyl)-1H-pyrazol-4-ylimino)-3-methylsulphonamidocyclohexa-2,5-dienylidene)hydroxy-methylpyrrolidinium, 1-(4-(5-amino-1-(2-hydroxyethyl)-1H-pyrazol-4-ylimino)-3-methylsulphonamidocyclohexa-2,5-dienylidene)-3-hydroxypiperidinium, 1-(4-(5-amino-1-(2-hydroxyethyl)-1H-pyrazol-4-ylimino)-3-methylsulphonamidocyclohexa-2,5-dienylidene)-3-hydroxypyrrolidinium, 4-(4-(5-amino-1-(2-hydroxyethyl)-1H-pyrazol-4-ylimino)-3-methylsulphonamidocyclohexa-2,5-dienylidene)morpholinium, 1-(4-(5-amino-1-(2-hydroxyethyl)-1H-pyrazol-4-ylimino)-3-methylsulphon-amidocyclohexa-2,5-dienylidene)piperidinium, 1-(4-(5-amino-1-(2-hydroxyethyl)-1H-pyrazol-4-ylimino)-3-methylsulphonamidocyclohexa-2,5-dienylidene)-pyrrolidinium, (4-(5-amino-1-(4-methylphenyl)methyl-1H-pyrazol-4-ylimino)-3-ureidocyclohexa-2,5-dienylidene) dimethyl-ammonium, (4-(5-amino-1-(4-methylphenyl)methyl-1H-pyrazol-4-ylimino)-3-ureidocyclohexa-2,5-dienylidene)diethylammonium, (4-(5-amino-1-(4-methylphenyl)methyl-1H-pyrazol-4-ylimino)-3-ureidocyclohexa-2,5-dienylidene)di(2-hydroxyethyl)ammonium, 1-(4-(5-amino-1-(4-methylphenyl)methyl-1H-pyrazol-4-ylimino)-3-ureidocyclohexa-2,5-dienylidene)-4-(hydroxy-methyl)piperidinium, 1-(4-(5-amino-1-(4-methylphenyl)-methyl-1H-pyrazol-4-ylimino)-3-ureidocyclohexa-2,5-dienylidene)-3-(hydroxymethyl)pyrrolidinium, 1-(4-(5-amino-1-(4-methylphenyl)methyl-1H-pyrazol-4-ylimino)-3-ureidocyclohexa-2,5-dienylidene)-4-hydroxypiperidinium, 1-(4-(5-amino-1-(4-methylphenyl)methyl-1H-pyrazol-4-ylimino)-3-ureidocyclohexa-2,5-dienylidene)-3-hydroxypyrrolidinium, 4-(4-(5-amino-1-(4-methylphenyl)methyl-1H-pyrazol-4-ylimino)-3-ureidocyclohexa-2,5-dienylidene)morpholinium, 1-(4-(5-amino-1-(4-methylphenyl)methyl-1H-pyrazol-4-ylimino)-3-ureidocyclohexa-2,5-dienylidene)piperidinium, 1-(4-(5-amino-1-(4-methylphenyl)methyl-1H-pyrazol-4-ylimino)-3-ureidocyclohexa-2,5-dienylidene)pyrrolidinium, (4-(5-amino-1-(4-methylphenyl)methyl-1H-pyrazol-4-ylimino)-

3-methylsulphonamidocyclohexa-2,5-dienylidene)dimethylammonium, (4-(5-amino-1-(4-methylphenyl)methyl-1H-pyrazol-4-ylimino)-3-methyl-sulphonamidocyclohexa-2,5-dienylidene)diethylammonium, (4-(5-amino-1-(4-methylphenyl)methyl-1H-pyrazol-4-ylimino)-3-methylsulphonamidocyclohexa-2,5-dienyl-idene)di(2-hydroxyethyl)ammonium, 1-(4-(5-amino-1-(4-methylphenyl)methyl-1H-pyrazol-4-ylimino)-3-methyl-sulphonamidocyclohexa-2,5-dienylidene)-4-(hydroxymethyl)piperidinium, 1-(4-(5-amino-1-(4-methyl-phenyl) methyl-1H-pyrazol-4-ylimino)-3-methylsulphonamidocyclohexa-2,5-dienylidene)hydroxymethyl-pyrrolidinium, 1-(4-(5-amino-1-(4-methylphenyl)methyl-1H-pyrazol-4-ylimino)-3-methylsulphonamidocyclohexa-2,5-dienylidene)-3-hydroxypiperidinium, 1-(4-(5-amino-1-(4-methylphenyl)methyl-1H-pyrazol-4-ylimino)-3-methylsulphonamidocyclohexa-2,5-dienylidene) hydroxypyrrolidinium, 4-(4-(5-amino-1-(4-methylphenyl) methyl-1H-pyrazol-4-ylimino)-3-methyl-sulphonamidocyclohexa-2,5-dienylidene)morpholinium, 1-(4-(5-amino-1-(4-methylphenyl)methyl-1H-pyrazol-4-ylimino)-3-methylsulphonamidocyclohexa-2,5-dienylidene) piperidinium, 1-(4-(5-amino-1-(4-methylphenyl)methyl-1H-pyrazol-4-ylimino)-3-methylsulphonamidocyclohexa-2,5-dienylidene)pyrrolidinium, (4-(5-amino-1-isopropyl-1H-pyrazol-4-ylimino)-3-ureidocyclohexa-2,5-dienylidene) dimethylammonium, (4-(5-amino-1-isopropyl-1H-pyrazol-4-ylimino)-3-ureidocyclohexa-2,5-dienylidene) diethylammonium, (4-(5-amino-1-isopropyl-1H-pyrazol-4-ylimino)-3-ureidocyclohexa-2,5-dienylidene)di(2-hydroxyethyl)ammonium, 1-(4-(5-amino-1-isopropyl-1H-pyrazol-4-ylimino)-3-ureidocyclohexa-2,5-dienylidene)-2-(hydroxymethyl)piperidinium, 1-(4-(5-amino-1-isopropyl-1H-pyrazol-4-ylimino)-3-ureidocyclohexa-2,5-dienylidene)-3-(hydroxymethyl)-pyrrolidinium, 1-(4-(5-amino-1-isopropyl-1H-pyrazol-4-ylimino)-3-ureidocyclohexa-2,5-dienylidene)-4-hydroxypiperidinium, 1-(4-(5-amino-1-isopropyl-1H-pyrazol-4-ylimino)-3-ureidocyclohexa-2,5-dienylidene)-3-hydroxypyrrolidinium, 4-(4-(5-amino-1-isopropyl-1H-pyrazol-4-ylimino)-3-ureidocyclohexa-2,5-dienylidene)-morpholinium, 1-(4-(5-amino-1-isopropyl-1H-pyrazol-4-ylimino)-3-ureidocyclohexa-2,5-dienylidene)piperidinium, 1-(4-(5-amino-1-isopropyl-1H-pyrazol-4-ylimino)-3-ureidocyclohexa-2,5-dienylidene)pyrrolidinium, (4-(5-amino-1-isopropyl-1H-pyrazol-4-ylimino)-3-methylsulphonamidocyclohexa-2,5-dienylidene)dimethylammonium, (4-(5-amino-1-isopropyl-1H-pyrazol-4-ylimino)-3-methylsulphonamidocyclohexa-2,5-dienylidene)diethylammonium, (4-(5-amino-1-isopropyl-1H-pyrazol-4-ylimino)-3-methylsulphonamidocyclohexa-2,5-dienylidene)di(2-hydroxyethyl)ammonium, 1-(4-(5-amino-1-isopropyl-1H-pyrazol-4-ylimino)-3-methylsulphonamidocyclohexa-2,5-dienylidene)-4-(hydroxymethyl)piperidinium, 1-(4-(5-amino-1-isopropyl-1H-pyrazol-4-ylimino)-3-methyl-sulphonamidocyclohexa-2,5-dienylidene)hydroxymethyl-pyrrolidinium, 1-(4-(5-amino-1-isopropyl-1H-pyrazol-4-ylimino)-3-methylsulphonamidocyclohexa-2,5-dienylidene)-3-hydroxypiperidinium, 1-(4-(5-amino-1-isopropyl-1H-pyrazol-4-ylimino)-3-methylsulphonamidocyclohexa-2,5-dienylidene)-3-hydroxypyrrolidinium, 4-(4-(5-amino-1-isopropyl-1H-pyrazol-4-ylimino)-3-methylsulphonamidocyclohexa-2,5-dienylidene) morpholinium, N-[(6-[(5-amino-1-isopropyl-1H-pyrazol-4-yl]imino]-3-(3-hydroxy-1-pyrrolidiniumylidene)-1,4-cyclohexadien-1-yl]urea, N-(-3-[(aminocarbonylamino)-4-{[5-amino-1-isopropyl-1H-pyrazol-4-yl]imino}-2,5-cyclohexadien-1-ylidene)-2-hydroxy-N-(2-hydroxyethyl) ethaneaminium, 1-(4-(5-amino-1-isopropyl-1H-pyrazol-4-ylimino)-3-methylsulphonamidocyclohexa-2,5-dienylidene) piperidinium and 1-(4-(5-amino-1-isopropyl-1H-pyrazol-4-ylimino)-3-methylsulphonamidocyclohexa-2,5-dienylidene) pyrrolidinium.

The 4-(pyrazol-4-ylimino)cyclohexa-2,5-dienylidene-ammonium salts of the formula (I) according to the invention can be prepared using known synthesis methods. The synthesis of the compounds according to the invention can take place, for example, by an oxidative coupling of a substituted pyrazole of the formula (II) with an aryl compound of the formula (III),

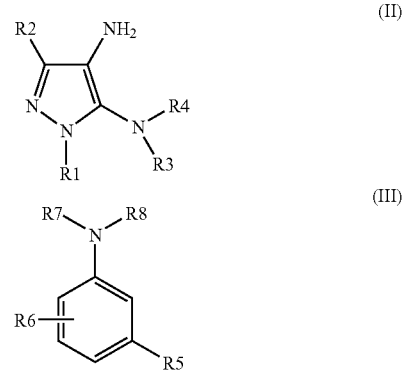

in which
R1, R2, R3, R4, R5, R6, R7 and R8 have the meaning given above.

The 4-(pyrazol-4-ylimino)cyclohexa-2,5-dienylidene-ammonium salts of the formula (I) according to the invention are readily soluble in water and permit colorations (including blue colorations) with high colour intensity and excellent colour fastness, in particular with regard to lightfastness, washing fastness and rubbing fastness. The compounds of the forms (I) also have excellent storage stability, especially as a constituent of the colorants described below.

The present invention therefore further provides agents for colouring keratin fibres, such as, for example, hair, furs, feathers or wool, in particular human hair, which are characterized in that they comprise at least one 4-(pyrazol-4-ylimino)cyclohexa-2,5-dienylidene-ammonium salt of the formula (I).

The compounds of the formula (I) are used in the agent according to the invention in a total amount of from about 0.005 to 20 per cent by weight, in particular 0.1 to 10 per cent by weight.

The compounds of the formula (I) colour keratinic material without the addition of further dyes in intense blue shades.

To expand the colour palette, the colorant according to the invention can additionally comprise further natural or synthetic nonoxidative dyes besides the dyes of the formula (I).

Natural dyes which may be mentioned are plant dyes, such as, for example, henna or indigo, while synthetic nonoxidative dyes which may be mentioned are azo dyes, triphenylmethane dyes, quinone dyes and, in particular, nitro dyes, such as, for example 1,4-bis[(2-hydroxyethyl)amino]-2-nitrobenzene, 1-(2-hydroxyethyl)-amino-2-nitro-4-[di(2-hydroxyethyl)amino]benzene (HC Blue No. 2), 1-amino-3-methyl-4-[(2-hydroxyethyl)-amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl) amino]-2-nitrobenzene (HC Blue No. 11), 1-[(2,3-dihydroxy-propyl)amino]-4-[methyl-(2-hydroxyethyl)amino]-2-nitrobenzene (HC Blue No. 10), 1-[(2,3-dihydroxy-propyl) amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl) amino]-2-nitrobenzene (HC Blue No. 6), 2-((4-amino-2-nitrophenyl)amino)-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)-amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl) amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl) amino]-2-nitrobenzene (HC Red No. 11), 2-[(2-hydroxyethyl)amino]-4,6-dinitrophenol, 4-ethylamino-3-nitro-benzoic acid, 2-[(4-amino-2-nitrophenyl)amino]-benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)-amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No.9), 1-[(2-ureidoethyl)amino]-4-nitrobenzene, 4-[(2,3-dihydroxy-propyl)amino]-3-nitro-1-trifluoromethylbenzene (HC Yellow No. 6), 1-chloro-2,4-bis[(2-hydroxyethyl)amino]-5-nitrobenzene (HC Yellow No. 10), 4-[(2-hydroxyethyl)-amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitro-benzonitrile (HC Yellow No. 14) and 4-[(2-hydroxy-ethyl) amino]-3-nitrobenzamide (HC Yellow No. 15).

Furthermore, besides the dyes of the formula (I), further cationic azo dyes, for example 1,4-dimethyl-5-[(4-(dimethylamino)phenyl)azo]-1,2,4-triazolium chloride (C.I. 11055; Basic Red 22), 1-methyl-4-{[methyl(phenyl)hydrazono] methyl}pyridinium chloride (Basic Yellow 87), 1-methyl-4-{(E)-[methyl(4-methoxy-phenyl)hydrazono] methyl}pyridinium chloride, 1-methyl-4-({methyl[4-methoxyphenyl]hydrazono}methyl)pyridinium methylsulphate (Basic Yellow 91), 2-{[4-(dimethyl-amino) phenyl]azo}-1,3-dimethyl-1H-imidazol-3-ium chloride (Basic Red 51), 5-{[4-(dimethylamino)-phenyl]azo}-1,2-dimethyl-1H-pyrazol-2-ium chloride, 1,3-dimethyl-2-{[4-(methylamino)phenyl]azo}-1H-imidazol-3-ium chloride (Basic Red 109), 2-[(4-aminophenyl)azo]-1,3-dimethyl-1H-imidazol-3-ium chloride, 4-{[4-(dimethylamino)phenyl] azo}-1-methyl-pyridinium chloride and N,N-dimethyl-4-[(E)-(1-oxido-4-pyridinyl)diazenyl]aniline, may also additionally be present.

The specified natural and synthetic direct dyes may be present in a total amount of from 0.001 to 4 per cent by weight.

Of course, oxidation dye precursors (developer substances, coupler substances), such as, for example, paraphenylenediamines, metaphenylenediamines, aminophenols or 4,5-diaminopyrazoles, can also be added to the colorant according to the invention.

These additional developer substances and coupler substances may be present in the colorant in each case in a total amount of from about 0.01 to 20 per cent by weight, preferably about 0.1 to 10% by weight and in particular 0.1 to 5% by weight.

The compounds according to formula (I) can in principle also serve to colour other natural fibres, such as, for example, cotton, jute, sisal, linen or silk, modified natural fibres, such as, for example, regenerated cellulose, nitrocellulose, alkylcellulose or hydroxyalkylcellulose or acetylcellulose, and synthetic fibres, such as, for example, polyamide fibres, polyurethane fibres or polyester fibres.

The compounds of the formula (I) can also serve for the simultaneous lightening and colouring of hair. For this, the direct dyes of the formula (I) are used together with an oxidizing agent.

Suitable oxidizing agents are primarily hydrogen peroxide or its addition compounds onto urea, melamine, sodium borate or sodium carbonate in the form of a 1 to 12 per cent strength, preferably a 3 to 6 per cent strength, aqueous solution. The weight ratio between colour carrier mass and oxidizing agent here is preferably about 5:1 to 1:3, in particular 1:1 to 1:2. Larger amounts of oxidizing agent are used if stronger bleaching of the keratin fibres (in particular of hair) is envisaged at the same time.

The preparation form of the hair colorant according to the invention can, for example, be a solution, in particular an aqueous or aqueous-alcoholic solution. However, the particularly preferred preparation forms are a cream, a gel, a surfactant-containing foaming solution (shampoo, aerosol), an emulsion or other water-containing carriers which are suitable for use on the hair. Their composition represents a mixture of the dye component with the additives customary for such preparations.

Customary additives in solutions, creams, emulsions or gels are, for example, solvents, such as water, lower aliphatic monohydric or polyhydric alcohols, and esters and ethers thereof, for example alkanols, in particular having 1 to 4 carbon atoms, for example ethanol, propanol or isopropanol, butanol, isobutanol, dihydric and trihydric alcohols, in particular those having 2 to 6 carbon atoms, for example ethylene glycol, propylene glycol, 1,3-propanediol, 1,4-butanediol, 1,5-pentane-diol, 1,6-hexanediol, 1,2,6-hexanetriol, glycerol, diethylene glycol, dipropylene glycol, polyalkylene glycols, such as triethylene glycol, polyethylene glycol, tripropylene glycol, polypropylene glycol, lower alkyl ethers of polyhydric alcohols, such as ethylene glycol monomethyl ether or ethylene glycol monoethyl ether or ethylene glycol monopropyl ether or ethylene glycol monobutyl ether, diethylene glycol monomethyl ether or diethylene glycol monoethyl ether, triethylene glycol monomethyl ether or triethylene glycol monoethyl ether, ketones and ketoalcohols, in particular those having 3 to 7 carbon atoms, such as, for example, acetone, methyl ethyl ketone, diethyl ketone, methyl isobutyl ketone, methyl phenyl ketone, cyclopentanone, cyclohexanone and diacetone alcohol, ethers, such as, for example, dibutyl ether, tetrahydrofuran, dioxane, diisopropyl ether, esters, such as, for example, ethyl formate, methyl formate, methyl acetate, ethyl acetate, propylene acetate, butyl acetate, phenyl acetate, ethylene glycol monoethyl ether acetate and hydroxyethyl acetate, amides, such as, for example, dimethylformamide and dimethylacetamide, N-methylpyrrolidone, and urea, tetramethylurea and thiodiglycol.

In addition, wetting agents or emulsifiers from the classes of anionic, cationic, amphoteric, nonionogenic or zwitterionic surface-active substances, such as fatty alcohol sulphates, alkanesulphonates, alkylbenzenesulphonates, alkyltrimethylammonium salts, alkylbetaines, α-olefinsulphonates, oxyethylated fatty alcohols, oxyethylated nonylphenols, fatty acid alkanolamines, oxyethylated fatty acid esters, fatty alcohol polyglycol ether sulphates, alkyl polyglucosides, thickeners, such as higher fatty alcohols, starch, cellulose derivatives, Vaseline, paraffin oil, fatty acids and other fatty components in emulsified form, water-soluble polymeric thickeners, such as natural gums, guar gum, xanthan gum, carob seed flour, pectin, dextran, agar agar, amylose, amylopectin, dextrins, clays or completely synthetic hydrocolloids, such as polyvinyl alcohol, also care substances such as lanolin derivatives, cholesterol, pantothenic acid, water-soluble cationic polymers, protein derivatives, provitamins, vitamins, plant extracts, sugars and betaine, auxiliaries such as humectants, electrolytes, antioxidants, fatty amides, sequestrants, film-forming agents and preservatives, may be present in the hair colorant according to the invention. Besides water, a water-soluble organic solvent or a mixture of such solvents and a water/solvent mixture may also be present.

The constituents mentioned are used in the amounts customary for such purposes, for example the wetting agents and emulsifiers in concentrations of from about 0.5 to 30 per cent by weight, the thickeners in an amount of from about 0.1 to 25 per cent by weight and the care substances in an amount of from about 0.1 to 5% by weight.

Depending on the composition, the colorants according to the invention may be weakly acidic, neutral or alkaline, acidic pHs preferably being established using citric acid, lactic acid, tartaric acid or phosphoric acid, while alkaline pHs are preferably established using ammonia. However, instead of ammonia, it is also possible to use other organic amines, such as, for example, monoethanolamine, diethanolamine, triethanol-amine, N-methyl-N-ethanolamine, N-methyl-N,N-diethanol-amine, 2-(2-hydroxyethoxy)ethanolamine, di-2-(2-hydroxyethoxy)ethaneamine and tri-2-(2-hydroxyethoxy)-ethaneamine or inorganic bases such as hydroxides, for example, lithium hydroxide, sodium hydroxide and potassium hydroxide, or carbonates, for example lithium carbonate, sodium carbonate or potassium carbonate.

The colouring solution is left to act on the hair at 20 to 50° C. for about 10 to 45 minutes, preferably at 40° C. for 40 minutes, then the hair is rinsed with water and dried. If necessary, this rinsing is followed by washing with a shampoo and/or after-rinsing with a weak organic acid. The hair is then dried.

The hair colorant according to the invention leads to hair colorations with excellent fastness properties, particularly with regard to lightfastness, washing fastness and rubbing fastness. The considerable colour intensity and the colour purity of the colorations which can be achieved is remarkable. Finally, using the hair colorant according to the invention, it is also possible to colour grey and chemically unpredamaged hair without problems and with very good coverage. The colorations obtained here, irrespective of the varying structure of the hair, are even and very readily reproducible.

The examples below are intended to illustrate the subject-matter of the invention in more detail without, however, limiting it thereto.

EXAMPLES

Example 1

Synthesis of 4-(5-aminopyrazol-4-ylimino)-cyclo-hexa-2,5-dienylidene-ammonium (General Synthesis Procedure)

0.01 mol of the corresponding pyrazole and 0.01 mol of the corresponding substituted meta-phenylenediamine are stirred in 30 ml of ethanol. The pH of the suspension is adjusted to 9 using a 30% strength aqueous ammonia solution. 12 ml of a 6% strength aqueous hydrogen peroxide solution are then added. The reaction mixture is stirred for 5 hours at room temperature. The reaction mixture is then filtered. The filtrate is treated with the saturated solution of a compound containing a negative counterion. The precipitate is filtered off, washed and then dried.

a. {4-[5-Amino-1-(2-hydroxyethyl)-1H-pyrazol-4-ylimino]-3-ureidocyclohexa-2,5-dienylidene}dimeth-ylammonium hydrogensulphate Pyrazole used: 4,5-diamino-1-(2-hydroxyethyl)-1H-pyrazole sulphate Phenylenediamine used: N-(3-Dimethylamino)phenyl) urea Compound with negative counterion used: potassium hydrogensulphate Yield: 2.4 g (58% of theory)

$^1$H-NMR: (500 MHz; $D_2O$) 7.88 ppm (1H, 3-H); 7.66 ppm (1H, 12-H, d, J=2.0 Hz); 7.49 ppm (1H, 15-H, J=10.0 Hz); 7.00 ppm (1H, 14-H, dd, J=2.1 Hz; 10.2 Hz); 4.24 ppm (2H, 6-H, t, J=5.3 Hz); 4.13 ppm (2H, 7-H, t, J=5.2 Hz); 3.52 ppm (6H, s, 2×$CH_3$).

b. {4-[5-Amino-1-isopropyl-1H-pyrazol-4-ylimino]-3-ureidocyclohexa-2,5-dienylidene}dimethylammonium hexafluorophosphate Pyrazole used: 4,5-diamino-1-isopropyl-1H-pyrazole sulphate Phenylenediamine used: N-(3-(dimethylamino)phenyl) urea Compound with negative counterion used: ammonium hexafluorophosphate Yield: 1.2 g (26% of theory)

1H-NMR (DMSO-d6): 1.37 (d, 6H); 3.34 (s, 6H); 4.58 (m, 1H); 6.79 (s, 2H); 6.88 (dd, 1H); 7.75 (d, 1H); 7.89 (s, 1H); 8.19 (b, 3H); 9.03 (s, 1H)

c. 1-{4-[5-Amino-1-isopropyl-1H-pyrazol-4-ylimino]-3-ureidocyclohexa-2,5-dienylidene}pyrrolidinium hexafluorophosphate Pyrazole used: 4,5-diamino-1-isopropyl-1H-pyrazole sulphate Phenylenediamine used: N-(3-(1-pyrrolidinyl)phenyl) urea Compound with negative counterion used: ammonium hexafluorophosphate Yield: 0.2 g (4% of theory)

1H-NMR (DMSO-d6): 1.37 (d, 6H); 3.35 (s, 6H); 4.58 (m, 1H); 6.79 (s, 2H) ; 6.88 (dd, 1H) ; 7.75 (d, 1H) ; 7.89 (s, 1H); 8.20 (b, 3H); 9.03 (s, 1H)

d. 4-{4-[5-Amino-1-isopropyl-1H-pyrazol-4-ylimino]-3-ureidocyclohexa-2,5-dienylidene}morpholinium hexafluorophosphate Pyrazole used: 4,5-diamino-1-isopropyl-1H-pyrazole sulphate
Phenylenediamine used: N-(3-(4-morpholinyl)phenyl)urea
Compound with negative counterion used: ammonium hexa-fluorophosphate
Yield: 1.35 g (27% of theory)
1H-NMR (DMSO-d6): 1.35 (d, 6H); 3.73 (m, 8H); 4.55 (m, 1H); 6.75 (s, 2H); 6.92 (d, 1H); 7.71 (d, 1H); 8.00 (s, 1H); 8.16 (s, 1H), 8.58 (b, 2H); 8.95 (s, 1H)

e. 1-(4-(5-Amino-1-isopropyl-1H-pyrazol-4-ylimino)-3-ureidocyclohexa-2,5-dienylidene)piperidinium hexa-fluorophosphate Pyrazole used: 4,5-diamino-1-isopropyl-1H-pyrazole sulphate
Phenylenediamine used: N-(3-(4-piperidinyl)phenyl)urea
Compound with negative counterion used: ammonium hexa-fluorophosphate
Yield: 1.35 g (27% of theory)
$^1$H-NMR (DMSO-d6): 1.35 (d, 6H), 1.69 (s, 6H), 3.71 (s, 4H), 4.58 (m, 1H), 6.77 (s, 2H), 6.95 (d, 1H), 7.70 (d, 1H), 8.08 (d, 2H), 8.55 (m, 1H), 8.98 (s, 1H)

f. 1-(4-(5-amino-1-isopropyl-1H-pyrazol-4-ylimino)-3-ureidocyclohexa-2,5-dienylidene)-3-hydroxy-pyrrolidinium hexafluorophosphate Pyrazole used: 4,5-diamino-1-isopropyl-1H-pyrazole sulphate
Phenylenediamine used: N-(3-(3-(3-hydroxypyrrolidinyl)-phenyl)urea
Compound with negative counterion used: ammonium hexafluorophosphate
Yield: 1.35 g (27% of theory)
$^1$H-NMR (DMSO-d6): 1.31 (d, 6H); 2.00 (m, 2H); 3.68 (s, 4H); 4.46 (s, 2H); 4.76 (1, 1H); 5.19 (s,1H); 6.57 (d, 2H); 7.70 (d, 2H); 8.04 (s, 1H); 9.27 (m, 2H)

g. (4-(5-amino-1-isopropyl-1H-pyrazol-4-ylimino)-3-ureidocyclohexa-2,5-dienylidene)di(2-hydroxyethyl)ammonium hexafluorophosphate Pyrazole used: 4,5-diamino-1-isopropyl-1H-pyrazole sulphate
Phenylenediamine used: N-(3-(3-(di(2-hydroxyethyl)amino)phenyl)urea
Compound with negative counterion used: ammonium hexafluorophosphate
Yield: 1.35 g (27% of theory)
$^1$H-NMR (DMSO-d6): 1.36 (d, 6H); 3.55 (dd, 8H); 4.58 (m, 1H) ; 6.76 (s, 2H); 6.96 (dd, 2H); 7.13 (d, 1H); 7.98 (d, 1H); 8.19 (s, 1H); 9.03 (s, 1H)

h. {4-[5-Amino-1-((4-methylphenyl)methyl)-1H-pyrazol-4-ylimino]-3-ureidocyclohexa-2,5-dienylidene}-dimethylammonium sulphate Pyrazole used: 4,5-diamino-1-(4-methylphenyl)methyl)-1H-pyrazole sulphate
Phenylenediamine used: N-(3-(3-(di(2-hydroxyethyl)-amino)phenyl)urea
Compound with negative counterion used: ammonium hexafluorophosphate
$^1$H-NMR (D$_2$O): 7.7 ppm (1H); 7.4-7.1 ppm (5H, m); 6.8-6.6 ppm (2H, m); 5.0 ppm (2H, s); 3.3 ppm (3H, s); 2.8 ppm (3H, s); 2.3 ppm (3H, s)

Examples 2 to 9

Hair Colorants

| 2.5 mmol | dye of the formula (I) as in Table 1 |
| 10.0 g | ethanol |
| 10.0 g | cetylstearyl alcohol |
| 1.0 g | benzyl alcohol |
| ad 100.0 g | water |

The above ready-to-use hair colorant is obtained directly prior to application by mixing the dye with the remaining components. The pH is adjusted either with lactic acid or with dilute ammonia solution. Bleached hair is then treated for 40 minutes at a temperature of 40° C. with the hair colorants (rendered acidic with lactic acid or rendered basic with dilute ammonia solution). The hair is then rinsed with water and dried. The hair has been given an intense coloration. The colouring results are summarized in Table 1.

TABLE 1

| Ex. | Dye of the formula (I) | Coloration obtained |
|---|---|---|
| 2 | {4-[5-Amino-1-(2-hydroxyethyl)-1H-pyrazol-4-ylimino]-3-ureidocyclohexa-2,5-dienylidene}dimethylammonium hydrogensulphate | dark blue |
| 3 | {4-[5-Amino-1-isopropyl-1H-pyrazol-4-ylimino]-3-ureidocyclohexa-2,5-dienylidene}dimethylammonium hexafluorophosphate | dark blue |
| 4 | 1-{4-[5-Amino-1-isopropyl-1H-pyrazol-4-ylimino]-3-ureidocyclohexa-2,5-dienylidene}pyrrolidinium hexafluorophosphate | dark blue |
| 5 | 4-{4-[5-Amino-1-isopropyl-1H-pyrazol-4-ylimino]-3-ureidocyclohexa-2,5-dienylidene}morpholinium hexafluorophosphate | dark blue |
| 6 | 1-(4-(5-Amino-1-isopropyl-1H-pyrazol-4-ylimino)-3-ureidocyclohexa-2,5-dienylidene)piperidinium hexafluorophosphate | dark blue |
| 7 | E. 1-(4-(5-Amino-1-isopropyl-1H-pyrazol-4-ylimino)-3-ureidocyclohexa-2,5-dienylidene)-3-hydroxypyrrolidinium hexafluorophosphate | dark blue |
| 8 | 4-(5-Amino-1-isopropyl-1H-pyrazol-4-ylimino)-3-ureidocyolohexa-2,5-dienylidene)di(2-hydroxyethyl)ammonium hexafluorophosphate | dark blue |
| 9 | {4-[5-Amino-1-((4-methylphenyl)methyl)-1H-pyrazol-4-ylimino]-3-ureidocyclohexa-2,5-dienylidene}dimethylammonium sulphate | dark blue |

Examples 10 to 17

Hair Colorant

| 0.0015 g | dye of the formula (I) as in Table 2 |
| 0.0600 g | 5-chloro-4-((2-hydroxyethyl)amino)-2-nitroaniline |

-continued

| | |
|---|---|
| 0.0250 g | 1-((4-amino-2-nitrophenyl)azo)-7-(tri-methylammonium)-2-naphthol chloride |
| 0.0300 g | 4-(di(2-hydroxyethyl)amino)-2-nitro-aniline |
| 10.000 g | ethanol |
| 10.000 g | cetylstearyl alcohol |
| ad 100.000 g | water |

The pH of the colouring solution is adjusted to 8 with dilute ammonia solution.

The above ready-to-use hair colorant is obtained directly prior to use by mixing the dye with the remaining components. Bleached hair is then treated for 40 minutes at a temperature of 40° C. with the hair colorant. The hair is then rinsed with water and dried. The colouring results are summarized in Table 2.

TABLE 2

| Ex. | Dye of the formula (I) | Coloration obtained |
|---|---|---|
| 10 | {4-{5-Amino-1-(2-hydroxyethyl)-1H-pyrazol-4-ylimino]-3-ureidocyclohexa-2,5-dienylidene}dimethylammonium hydrogensulphate | blonde |
| 11 | {4-[5-Amino-1-isopropyl-1H-pyrazol-4-ylimino]-3-ureidocyclohexa-2,5-dienylidene}dimethylammonium hexafluorophosphate | blonde |
| 12 | 1-{4-[5-Amino-1-isopropyl-1H-pyrazol-4-ylimino]-3-ureidocyclohexa-2,5-dienylidene}pyrrolidinium hexafluorophosphate | blonde |
| 13 | 4-{4-[5-Amino-1-isopropyl-1H-pyrazol-4-ylimino]-3-ureidocyclohexa-2,5-dienylidene}morpholinium hexafluorophosphate | blonde |
| 14 | 1-(4-(5-Amino-1-isopropyl-1H-pyrazol-4-ylimino)-3-ureidocyclohexa-2,5-dienylidene)piperidinium hexafluorophosphate | blonde |
| 15 | N-[(6-[(5-Amino-1-isopropyl-1H-pyrazol-4-yl)imino]-3-(3-hydroxy-1-pyrrolidiniumylidene)-1,4-cyclohexadien-1-yl]urea hexafluorophosphate | blonde |
| 16 | N-(-3-[(Aminocarbonyl)amino]-4-{[5-amino-1-isopropyl-1H-pyrazol-4-yl]imino}-2,5-cyclohexadien-1-ylidene)-2-hydroxy-N-(2-hydroxyethyl)ethaneaminium hexafluorophosphate | blonde |
| 17 | {4-[5-Amino-1-((4-methylphenyl)methyl)-1H-pyrazol-4-ylimino]-3-ureidocyclohexa-2,5-dienylidene}dimethylammonium sulphate | blonde |

Examples 18 to 25

Hair Colorants

| | |
|---|---|
| 2.3 mmol | dye of the formula (I) as in Table 3 |
| 0.260 g | 4-(ethyl(2-hydroxyethyl)amino)-N-(2-hydroxyethyl)-2-nitroaniline hydrochloride |
| 0.090 g | N-(2-hydroxyethyl)-4-methyl-2-nitroaniline |
| 0.080 g | 5-chloro-4-((2,3-dihydroxypropyl)amino)-2-nitroaniline |
| 0.170 g | 1-((4-amino-2-nitrophenyl)azo)-7-(trimethylammonium)-2-naphthol chloride |
| 0.016 g | di(4-diethylamino)phenyl)(4-(ethyl-amino) naphthyl)carbenium chloride |
| 10.000 g | ethanol |
| 10.000 g | cetylstearyl alcohol |
| ad 100.000 g | water |

The pH of the colouring solution is adjusted to 8 with dilute ammonia solution.

The above ready-to-use hair colorant is obtained directly prior to use by mixing the dye of the formula (I) with the remaining components. Bleached hair is then treated for 40 minutes at a temperature of 40° C. with the hair colorant. The hair is then rinsed with water and dried.

The colouring results are summarized in Table 3.

TABLE 3

| Ex. | Dye of the formula (I) | Coloration obtained |
|---|---|---|
| 18 | {4-[5-Amino-1-(2-hydroxyethyl)-1H-pyrazol-4-ylimino]-3-ureidocyclohexa-2,5-dienylidene}dimethylammonium hydrogensulphate | brown |
| 19 | {4-[5-Amino-1-isopropyl-1H-pyrazol-4-ylimino]-3-ureidocyclohexa-2,5-dienylidene}dimethylammonium hexafluorophosphate | brown |
| 20 | 1-{4-[5-Amino-1-isopropyl-1H-pyrazol-4-ylimino]-3-ureidocyclohexa-2,5-dienylidene}pyrrolidinium hexafluorophosphate | brown |
| 21 | 4-{4-[5-Amino-1-isopropyl-1H-pyrazol-4-ylimino]-3-ureidocyclohexa-2,5-dienylidene}morpholinium hexafluorophosphate | brown |
| 22 | 1-(4-(5-Amino-1-isopropyl-1H-pyrazol-4-ylimino)-3-ureidocyclohexa-2,5-dienylidene)piperidinium hexafluorophosphate | brown |
| 23 | E. 1-(4-(5-amino-1-isopropyl-1H-pyrazol-4-ylimino)-3-ureidocyclohexa-2,5-dienylidene)-3-hydroxypyrrolidinium hexafluorophosphate | brown |
| 24 | (4-(5-Amino-1-isopropyl-1H-pyrazol-4-ylimino)-3-ureidocyclohexa-2,5-dienylidene)di(2-hydroxy-ethyl)ammonium hexafluorophosphate | brown |
| 25 | {4-[5-Amino-1-((4-methylphenyl)methyl)-1H-pyrazol-4-ylimino]-3-ureidocyclohexa-2,5-dienylidene}dimethylammonium sulphate | blonde |

Examples 26 to 33

Hair Colorants

| | |
|---|---|
| 0.0020 g | dye of the formula (I) as in Table 4 |
| 0.0005 g | di(4-aminophenyl)(4-amino-3-methyl-phenyl) carbenium chloride |
| 10.0000 g | isopropanol |
| 1.0000 g | benzyl alcohol |
| 10.0000 g | cetylstearyl alcohol |
| ad 100.0000 g | water |

The above ready-to-use hair colorant is obtained directly prior to use by mixing the dye with the remaining components. The pH is adjusted either with lactic acid or with dilute ammonia solution. Bleached hair is then treated for 40 minutes at a temperature of 40° C. with the hair colorant. The hair is then rinsed with water and dried.

The colouring results are summarized in Table 4.

TABLE 4

| Ex. | Dye of the formula (I) | Coloration obtained |
|---|---|---|
| 26 | {4-[5-Amino-1-(2-hydroxyethyl)-1H-pyrazol-4-ylimino]-3-ureidocyclohexa-2,5-dienylidene}dimethylammonium hydrogensulphate | silver grey |
| 27 | {4-[5-Amino-1-isopropyl-1H-pyrazol-4-ylimino]-3-ureidocyclohexa-2,5-dienylidene}dimethylammonium hexafluorophosphate | silver grey |
| 28 | 1-{4-[5-Amino-1-isopropyl-1H-pyrazol-4-ylimino]-3-ureidocyclohexa-2,5-dienylidene}pyrrolidinium hexafluorophosphate | silver grey |
| 29 | 4-{4-[5-Amino-1-isopropyl-1H-pyrazol-4-ylimino]-3-ureidocyclohexa-2,5-dienylidene}morpholinium hexafluorophosphate | silver grey |
| 30 | 1-(4-(5-Amino-1-isopropyl-1H-pyrazol-4-ylimino)-3-ureidocyclohexa-2,5-dienylidene)piperidinium hexafluorophosphate | silver grey |
| 31 | E. 1-(4-(5-Amino-1-isopropyl-1H-pyrazol-4-ylimino)-3-ureidocyclohexa-2,5-dienylidene)-3-hydroxypyrrolidinium hexafluorophosphate | silver grey |
| 32 | (4-(5-Amino-1-isopropyl-1H-pyrazol-4-ylimino)-3-ureidocyclohexa-2,5-dienylidene)di(2-hydroxyethyl)ammonium hexafluorophosphate | silver grey |
| 33 | {4-[5-Amino-1-((4-methylphenyl)methyl)-1H-pyrazol-4-ylimino]-3-ureidocyclohexa-2,5-dienylidene}dimethylammonium sulphate | silver grey |

Examples 34 to 41

Hair Colorants

| | |
|---|---|
| 1.000 g | dye of the formula (I) as in Table 5 |
| 2.800 g | steareth-20 |
| 12.000 g | cetylstearyl alcohol |
| 20.000 g | ethanol |
| ad 100.000 g | water |

The pH is adjusted to 10 with 25% strength ammonia.

5 g of the above colour carrier mass are mixed with 7.5 g of a 9% strength hydrogen peroxide solution. The resulting ready-to-use hair colorant is applied to hair tresses and distributed evenly using a brush. After a contact time of 30 minutes at 40° C., the hair is rinsed with lukewarm water, washed with shampoo, rinsed with lukewarm water and then dried. The colouring results are summarized in Table 5.

Unless stated otherwise, all of the weights given are percentages by weight.

TABLE 5

| Ex. | Dye of the formula (I) | Coloration obtained |
|---|---|---|
| 34 | {4-[5-Amino-1-(2-hydroxyethyl)-1H-pyrazol-4-ylimino]-3-ureidocyclohexa-2,5-dienylidene}dimethylammonium hydrogensulphate | blue |
| 35 | {4-[5-Amino-1-isopropyl-1H-pyrazol-4-ylimino]-3-ureidocyclohexa-2,5-dienylidene}dimethylammonium hexafluorophosphate | blue |
| 36 | 1-{4-[5-Amino-1-isopropyl-1H-pyrazol-4-ylimino]-3-ureidocyclohexa-2,5-dienylidene}pyrrolidinium hexafluorophosphate | blue |
| 37 | 4-{4-[5-Amino-1-isopropyl-1H-pyrazol-4-ylimino]-3-ureidocyclohexa-2,5-dienylidene}morpholinium hexafluorophosphate | blue |
| 38 | N-[6-[(5-Amino-1-isopropyl-1H-pyrazol-4-yl)imino]-3-(1-piperidiniumylidene)-1,4-cyclohexadien-1-yl] urea hexafluorophosphate | blue |
| 39 | 1-(4-(5-Amino-1-isopropyl-1H-pyrazol-4-ylimino)-3-ureidocyclohexa-2,5-dienylidene)-3-hydroxypyrrolidinium hexafluorophosphate | blue |
| 40 | (4-(5-Amino-1-isopropyl-1H-pyrazol-4-ylimino)-3-ureidocyclohexa-2,5-dienylidene)di(2-hydroxyethyl)ammonium hexafluorophosphate | blue |
| 41 | {4-[5-Amino-1-((4-methylphenyl)methyl)-1H-pyrazol-4-ylimino]-3-ureidocyclohexa-2,5-dienylidene}dimethylammonium sulphate | blue |

The invention claimed is:

1. 4-(Pyrazol-4-ylimino)-2,5-cyclohexadienylidene-ammonium salt of the general formula (I)

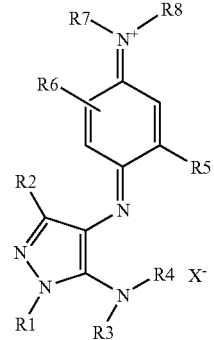

in which
R1 is a $C_1$-$C_6$-alkyl group, a $C_1$-$C_4$-hydroxyalkyl group, a $C_2$-$C_4$-dihydroxyalkyl group or a $C_2$-$C_6$-alkoxy-($C_1$-$C_2$)-alkyl group, a phenyl group, a benzyl group or a substituted benzyl group;

R3 and R4, independently of one another, are hydrogen, a $C_1$-$C_6$-alkyl group, a $C_1$-$C_4$-hydroxyalkyl group, a $C_2$-$C_4$-dihydroxyalkyl group or a $C_1$-$C_4$-alkoxy-($C_1$-$C_4$)alkyl group, or R3 and R4 together form a four-membered to eight-membered aliphatic ring;

R2 and R6, independently of one another, are hydrogen, a $C_1$-$C_4$-alkyl group, a $C_1$-$C_4$-hydroxyalkyl group, a phenyl group, a substituted phenyl group, a halogen atom or a substituted aminomethyl group;

R5 is a cyano group, a —NR10C(O)R11 group or a sulphonamide group;

R7 and R8, independently of one another, are a $C_1$-$C_6$-alkyl group, an unsaturated $C_3$-$C_6$-alkyl group, a $C_2$-$C_4$-hydroxyalkyl group, a $C_3$-$C_4$-dihydroxyalkyl group, a $C_2$-$C_4$-aminoalkyl group, a $C_2$-$C_4$-dimethylaminoalkyl group, a $C_2$-$C_4$-acetylaminoalkyl group, a $C_2$-$C_4$-methoxyalkyl group, a $C_2$-$C_4$-ethoxyalkyl group, a $C_1$-$C_4$-cyanoalkyl group, a $C_1$-$C_4$-carboxyalkyl group or a $C_1$-$C_4$-aminocarbonylalkyl group, or R7 and R8, together with the nitrogen atom, form a ring of the formula

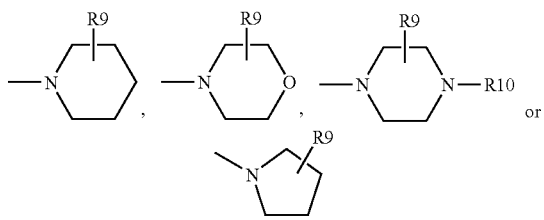

R9 is hydrogen or one or more hydroxyl groups, carboxyl groups, aminocarbonyl groups or hydroxymethyl groups;
R10 is hydrogen or a $C_1$-$C_6$-alkyl group;
R11 is hydrogen, a $C_1$-$C_6$-alkyl group, an amino group, an alkylamino group, a dialkylamino group, a phenyl group or a substituted phenyl group; and
$X^-$ is an anion.

2. 4 (Pyrazol-4-ylimino)-2,5-cyclohexadienylidene-ammonium salt according to claim 1, characterized in that one or more of the radicals R2, R3, R4 and R6 are hydrogen.

3. 4-(Pyrazol-4-ylimino)-2,5-cyclohexadienylidene-ammonium salt according to claim 1, characterized in that R1 is a $C_1$-$C_6$-alkyl group, a $C_1$-$C_4$-hydroxyalkyl group, a benzyl group or methylbenzyl group and R2, R3, R4 and R6 are hydrogen at the same time.

4. 4-(Pyrazol-4-ylimino)-2,5-cyclohexadienylidene-ammonium salt according to claim 1, characterized in that R5 is an amino group, a —NHC (O)R11 group or a sulphonamide group and R6 is hydrogen.

5. 4-(Pyrazol-4-ylimino)-2,5-cyclohexadienylidene-ammonium salt according to claim 1, characterized in that, in the formula(I), the radicals R7 and R8 are a $C_1$-$C_3$-alkyl group — in particular a methyl group — or, together with the nitrogen atom, form a pyrrolidine ring.

6. 4-(Pyrazol-4-ylimino)-2,5-cyclohexadienylidene-ammonium according to claim 1, characterized in that it is chosen from(4-(5-amino-1-(2-hydroxyethyl)-1H-pyrazol-4-ylimino)-3-ureidocyclohexa-2,5-dienylidene) dimethylammonium, (4-(5-amino-1-(2-hydroxyethyl)-1H-pyrazol-4-ylimino)-3-ureidocyclohexa-2,5-dienylidene) diethylammonium, (4-(5-amino-1-(2-hydroxyethyl)-1H-pyrazol-4-ylimino)-3-ureidocyclohexa-2,5-dienylidene)di(2-hydroxyethyl)ammonium, 1-(4-(5-amino-1-(2-hydroxyethyl)-1H-pyrazol-4-ylimino)-3-ureidocyclohexa-2,5-dienylidene )-4-(hydroxymethyl) -piperidinium, 1-(4-(5-amino-1-(2-hydroxyethyl)-1H-pyrazol -4-ylimino)-3-ureidocyclohexa-2,5-dienylidene)hydroxymethyl -pyrrolidinium, 1-(4-(5-amino-1-(2-hydroxyethyl)-1H-pyrazol -4-ylimino)-3-ureidocyclohexa-2,5-dienylidene)-4-hydroxypiperidinium, 1-(4-(5-amino-1-(2-hydroxyethyl)-1H -pyrazol-4-ylimino)-3-ureidocyclohexa-2,5-dienylidene)-3-hydroxypyrrolidinium, (4-(5-amino-1-(2-hydroxyethyl)-1H -pyrazol-4-ylimino)-3-ureidocyclohexa-2,5-dienylidene) morpholinium, 1-(4-(5-amino-l-(2-hydroxyethyl) -1H-pyrazol-4-ylimino)-3-ureidocyclohexa-2,5-dienylidene)piperidinium, 1-(4-(5-amino-l-(2-hydroxyethyl) -1H-pyrazol-4-ylimino)-3-ureidocyclohexa-2,5-dienylidene)pyrrolidinium, (4-(5-amino-l-(2-hydroxyethyl) -1H-pyrazol-4-ylimino)-3-methylsulphonamidocyclohexa-2,5-dienylidene)dimethylammonium, (4-(5-amino-1-(2-hydroxyethyl)-1H-pyrazol-4-ylimino)-3-methylsulphonamidocyclohexa-2,5-dienylidene)diethylammonium, (4-(5-amino-1-(2-hydroxyethyl)-1H-pyrazol-4-ylimino)-3-methylsulphonamidocyclohexa-2,5-dienylidene)di(2-hydroxyethyl)ammonium, 1-(4-(5-amino-1-(2-hydroxyethyl)-1H -pyrazol-4-ylimino)-3-methylsulphonamidocyclohexa-2,5-dienylidene) hydroxymethylpiperidnium, 1-(4-(5-amino-1-(2-hydroxyethyl)-1H-pyrazol-4-ylimino)-3-methylsulphonamidocyclohexa-2,5-dienylidene) hydroxymethylpyrroldinium, 1-(4-(5-amino-1-(2-hydroxyethyl)-1H-pyrazol-4-ylimino)-3-methylsulphonamidocyclohexa-2,5-dienylidene)-3-hydroxypiperidinium, 1-(4-(5-amino-1-(2-hydroxyethyl)-1-pyrazol-4-ylimino)-3-methylsulphonamidocyclohexa-2,5-dienylidene)-3-hydroxypyrrolidinium, 4-(4-(5-amino-1-(2-hydroxyethyl)-1H-pyrazol-4-ylimino)-3-methylsulphon -amidocyclohexa-2,5-dienylidene)morpholinium, 1-(4-(5-amino -1-(2hydroxyethyl)-1-H-pyrazol-4-ylimino)-3-methylsulphonamidocyclohexa-2,5-dienylidene)piperidinium, 1-(4-(5-amino-1-(2-hydroxyethyl)-1-H-pyrazol-4-ylimino)-3-methylsulphonamidocyclohexa-2,5-dienylidene)pyrrolidinium, (4-(5-amino-1-(4-methylphenyl)methyl-1H-pyrazol-4-ylimino) -3-ureidocyclohexa-2,5-dienylidene) dimethylammonium, (4-(5-amino-1-(4-methylphenyl) methyl-1H-pyrazol-4-ylimino)-3-ureidocyclohexa-2,5-dienylidene)diethylammonium, (4-(5-amino-1-(4-methylphenyl)methyl-1H-pyrazol-4-ylimino)-3-ureidocyclohexa-2,5-dienylidene)di(2-hydroxy-ethyl) ammonium, 1-(4-(5-amino-1-(4-methylphenyl)methyl-1H-pyrazol-4-ylimino)-3-ureidocyclohexa-2,5-dienylidene)-4-(hydroxymethyl)piperidinium, 1-(4-(5-amino-1-(4-methylphenyl)methyl-1H-pyrazol-4ylimino)-3-ureidocyclohexa-2,5-dienylidene)-3-(hydroxymethyl) pyrrolidinium, 1-(4-(5-amino-1-(4-methylphenyl)methyl-1H-pyrazol-4ylimino)-3-ureidocyclohexa-2,5-dienylidene)-4-hydroxypiperidinium, 1-(4-(5-amino-1-(4-methylphenyl) methyl-1H-pyrazol-4-ylimino)-3-ureidocyclohexa-2,5-dienylidene)-3-hydroxypyrrolidinium, 4-(4-(5-amino-1-(4-methylphenyl)methyl-1H-pyrazol-4-ylimino)-3-ureidocyclohexa-2,5-dienylidene)morpholinium, 1-(4-(5-amino-1-(4-methylphenyl)methyl-1H-pyrazol-4-ylimino)-3-ureidocyclohexa-2,5-dienylidene)piperidinium, 1-(4-(5-amino-1-(4-methylphenyl)methyl-1H-pyrazol-4-ylimino)-3-ureidocyclohexa-2,5-dienylidene)pyrrolidinium, (4-(5-amino-1-(4-methylphenyl)methyl-1H-pyrazol-4-ylimino)-3-methylsulphonamidocyclohexa-2,5-dienylidene) dimethylammonium, (4-(5-amino-1-(4-methylphenyl) methyl-1H-pyrazol-4-ylimino)-3-methylsulphonamidocyclohexa-2,5-dienylidene) diethylammonium, (4-(5-amino-1-(4-methylphenyl)methyl-1H-pyrazol-4-ylimino)-3-methylsulphonamidocyclohexa-2,5-dienylidene)di(2-hydroxyethyl)ammonium, 1-(4-(5-amino-1-(4-methylphenyl)methyl-1H-pyrazol-4-ylimino)-3-methyl -sulphonamidocyclohexa-2,5-dienylidene) hydroxymethyl -piperidinium, 1-(4-(5-amino-1-(4-methylphenyl)methyl-1H -pyrazol-4-ylimino)-3-methylsulphonamidocyclohexa-2,5-dienylidene) hydroxymethylpyrrolidinium, 1-(4-(5-amino-1-(4-methylphenyl)methyl-1H-pyrazol-4-ylimino)-3-methylsulphonamidocyclohexa-2,5-dienylidene)-4-hydroxypiperidinium, 1-(4-(5-amino-1-(4-methyl -phenyl) methyl-1H-pyrazol-4-ylimino)-3-methylsulphon -amidocyclohexa-2,5-dienylidene)-3-hydroxypyrrolidinium, (4-(5-amino-1-(4-methylphenyl)methyl-1H-pyrazol-4-ylimino)-3-methylsulphonamidocyclohexa-2,5-dienylidene)morpholinium, 1-(4-(5-amino-1-(4-methylphenyl)methyl-1H-pyrazol-4-ylimino)-3-methylsulphonamidocyclohexa-2,5-dienylidene) piperidinium, 1-(4-(5-amino-1-(4-methylphenyl) -methyl- 1H-pyrazol-4-ylimino)-3-methylsulphonamidocyclohexa-2,5-dienylidene)-pyrrolidinium, (4-(5-amino-1-isopropyl-1H-pyrazol-4-ylimino)-3-ureidocyclohexa-2,5-dienylidene)dimethylammonium, (4-(5-amino-1-isopropyl-1H-pyrazol-4-ylimino)-3-ureidocyclohexa-2,5-dienylidene)diethylammonium, (4-(5-amino-1-isopropyl-1H-pyrazol-4-ylimino)-3-ureidocyclohexa-2,5-dienylidene)di(2-hydroxyethyl)ammonium, 1-(4-(5-amino-1-isopropyl-1H-pyrazol-4-ylimino)-3-ureidocyclohexa-2,5-dienylidene)-4-(hydroxymethyl)piperidinium, 1-(4-(5-amino-1-isopropyl-1H-pyrazol-4-ylimino)-3-ureidocyclohexa-2,5-dienylidene)-3-(hydroxymethyl)pyrrolidinium, 1-(4-(5-amino-1-isopropyl-1H-pyrazol-4-ylimino)-3-ureidocyclohexa-2,5-dienylidene)-3-hydroxypiperidinium, 1-(4-(5-amino-1-isopropyl-1H-pyrazol-4-ylimino)-3-ureidocyclohexa-2,5-dienylidene)-3-hydroxypyrrolidinium, 4-(4-(5-amino-1-isopropyl-1H-pyrazol-4-ylimino)-3-ureidocyclohexa-2,5-dienylidene)morpholinium, 1-(4-(5-amino-1-isopropyl-1H-pyrazol-4-ylimino)-3-ureidocyclohexa-2,5-dienylidene)piperidinium, 1-(4-(5-amino-1-isopropyl-1H-pyrazol-4-ylimino)-3-ureidocyclohexa-2,5-dienylidene)pyrrolidinium, (4-(5-amino-1-isopropyl-1H-pyrazol-4-ylimino)-3-methylsulphonamidocyclohexa-2,5-dienylidene)dimethylammonium, (4-(5-amino-1-isopropyl-1H-pyrazol-4-ylimino)-3-methylsulphonamidocyclohexa-2,5-dienylidene)diethylammonium, (4-(5-amino-1-isopropyl-1H-pyrazol-4-ylimino)-3-methylsulphonamidocyclohexa-2,5-dienylidene)di(2-hydroxyethyl)ammonium, 1-(4-(5-amino-1-isopropyl-1H-pyrazol-4-ylimino)-3-methylsulphonamidocyclohexa-2,5-dienylidene)-4-(hydroxymethyl)piperidinium, 1-(4-(5amino-1-isopropyl-1H-pyrazol-4-ylimino)-3-methylsulphonamidocyclohexa-2,5-dienylidene)-3-(hydroxymethyl)pyrrolidinium, 1-(4-(5-amino-1-isopropyl-1H-pyrazol-4-ylimino)-3-methylsulphonamidocyclohexa-2,5-dienylidene)-4-hydroxypiperidinium, 1-(4-(5-amino-1-isopropyl-1H-pyrazol-4-ylimino)-3-methylsulphonamidocyclohexa-2,5-dienylidene)-3-hydroxypyrrolidinium, 4-(4-(5-amino-1-isopropyl-1H-pyrazol-4-ylimino)-3-methylsulphonamidocyclohexa-2,5-dienylidene)morpholinium, N-[(6-[(5-amino-1-isopropyl-1H-pyrazol-4-yl)imino]-3-(3-hydroxy-1-pyrrolidiniumylidene)-1,4-cyclohexadien-1-yl]urea, N-(-3-[(amino-carbonyl)amino]-4-{[5-amino-1-isopropyl-1H-pyrazol-4-yl]imino}-2,5-cyclohexadien-1-ylidene)-2-hydroxy-N-(2-hydroxyethyl)ethaneaminium, 1-(4-(5-amino-1-isopropyl-1H-pyrazol-4-ylimino)-3-methylsulphonamidocyclohexa-2,5-dienylidene)-piperidinium and 1-(4-(5-amino-1-isopropyl-1H-pyrazol-4-ylimino)-3-methylsulphonamidocyclohexa-2,5-dienylidene)pyrrolidinium.

7. Agent for colouring keratin fibres, characterized in that it comprises at least one 4-(pyrazol-4-ylimino)-2,5-cyclohexadienylidene-ammonium salt of the formula(I) according to claim 1.

8. Agent according to claim 7, characterized in that it comprises the 4-(pyrazol-4-ylimino)-2,5-cyclohexadienylidene-ammonium salt of the formula(I) in an amount of from 0.005 to 20% by weight.

9. Agent according to claims 7 agent, characterized in that it additionally comprises at least one further direct natural or synthetic hair dye and/or at least one oxidation dye precursor.

10. Agent according to claim 9, characterized in that the direct dyes are present in a total amount of from 0.001 to 4% by weight.

11. Agent according to claim 9, characterized in that the oxidation dye precursors are present in a total amount of from 0.01 to 20% by weight.

12. Agent for the simultaneous lightening and colouring of keratin fibres containing at least one oxidizing agent, characterized in that it comprises at least one 4-(pyrazol-4-ylimino)-2,5-cyclohexadienylidene-ammonium salt of the formula (I) according to claim 1.

13. Agent according to claim 12, characterized in that it has a basic pH.

14. Agent according to claim 11, characterized in that the oxidizing agent is hydrogen peroxide.

15. Agent according to claim 7, characterized in that it is a hair colorant.

* * * * *